United States Patent [19]

Ersfeld et al.

[11] Patent Number: 4,856,502

[45] Date of Patent: * Aug. 15, 1989

[54] CURABLE RESIN COATED SHEETS HAVING REDUCED TACK

[75] Inventors: Dean A. Ersfeld, Maplewood; Paul E. Hansen, Lake Elmo; Matthew T. Scholz; Dennis C. Bartizal, both of Woodbury; Katherine E. Reed, Stillwater; Wayne K. Larson, Maplewood, all of Minn.; Timothy C. Sandvig, Woodville, Wis.; Richard S. Buckanin, Woodbury, Minn.

[73] Assignee: Minnesota Mining and Manufacturing Company, St. Paul, Minn.

[*] Notice: The portion of the term of this patent subsequent to Jun. 27, 2006 has been disclaimed.

[21] Appl. No.: 53,098

[22] Filed: May 22, 1987

Related U.S. Application Data

[63] Continuation-in-part of Ser. No. 47,006, May 5, 1987, and Ser. No. 784,671, Oct. 4, 1985, Pat. No. 4,667,661.

[51] Int. Cl.$^4$ .............................................. A61F 5/04
[52] U.S. Cl. .................................. 128/90; 128/89 R; 427/2; 428/253; 428/423.1; 428/425.6; 428/913
[58] Field of Search ................ 128/89 R, 90, 91 R, 128/155, 156, 169; 427/2; 428/253, 290, 352, 423.1, 423.7, 425.6, 913

[56] References Cited

U.S. PATENT DOCUMENTS

| | | | |
|---|---|---|---|
| 3,043,298 | 7/1962 | Brickman et al. | 128/91 |
| 3,089,486 | 5/1963 | Pike | 128/90 |
| 3,332,416 | 7/1967 | Brickman et al. | 128/91 |
| 3,373,741 | 3/1968 | Hill et al. | 128/90 |
| 3,420,231 | 1/1969 | Edenbaum | 128/90 |
| 3,485,706 | 12/1969 | Evans | 161/72 |
| 3,630,194 | 12/1971 | Boardman | 128/90 |
| 3,681,184 | 3/1970 | Kalwaites | 161/109 |
| 3,682,756 | 3/1970 | Kalwaites | 161/109 |
| 3,763,858 | 10/1973 | Buese | 128/156 |
| 3,847,722 | 11/1974 | Kistner | 161/109 |
| 3,972,323 | 8/1976 | Boricheski | 128/91 R |
| 4,100,122 | 7/1978 | Kent | 260/28.5 |
| 4,238,522 | 12/1980 | Potts | 427/2 |
| 4,288,479 | 8/1981 | Brack | 428/40 |
| 4,376,438 | 3/1983 | Straube et al. | 128/90 |
| 4,383,079 | 5/1983 | Gasper et al. | 524/767 |
| 4,411,262 | 10/1983 | Von Bonin et al. | 128/90 |
| 4,414,275 | 11/1983 | Woods | 428/352 |
| 4,427,003 | 1/1984 | Fennimore et al. | 128/90 |
| 4,433,680 | 2/1984 | Yoon | 128/90 |
| 4,454,873 | 3/1985 | Laufenberg et al. | 128/90 |
| 4,502,479 | 3/1985 | Garwood et al. | 128/90 |
| 4,570,622 | 2/1986 | Von Bonin et al. | 128/90 |
| 4,609,578 | 9/1986 | Reed | 428/76 |
| 4,627,424 | 12/1986 | Baron et al. | 128/83 |
| 4,638,795 | 1/1987 | Richter et al. | 128/90 |
| 4,667,661 | 5/1987 | Scholz et al. | 128/90 |
| 4,705,840 | 11/1987 | Buckanin | 528/53 |

FOREIGN PATENT DOCUMENTS

| | | |
|---|---|---|
| 0094222 | 5/1983 | European Pat. Off. . |
| 3426732 | 1/1986 | Fed. Rep. of Germany ........ 128/90 |
| 54-100181 | 8/1979 | Japan . |
| 2021128 | 5/1979 | United Kingdom . |
| 2092606 | 8/1982 | United Kingdom . |

OTHER PUBLICATIONS

Isaacs, (brochure editor), "Textile World Manmade Fiber Chart", McGraw-Hill, (1986).

(List continued on next page.)

Primary Examiner—Richard J. Apley
Assistant Examiner—Paul Prebilic
Attorney, Agent, or Firm—Donald M. Sell; Walter N. Kirn; Dale E. Hulse

[57] ABSTRACT

The present invention relates to orthopedic casting materials having reduced tack and methods for preparing and using such orthopedic casting materials, wherein the materials comprise a nonwoven, stretchable fabric which is impregnated with a curable prepolymer resin. The nonwoven fabric comprises fiber bundles and apertures between the fiber bundles, with each of the fiber bundles comprising a plurality of fibers having interstices therebetween. The curable prepolymer resin is impregnated into the nonwoven fabric such that the interstices between the fibers receive the resin, while leaving the apertures between fiber bundles substantially unoccluded. Such orthopedic casting materials are relatively inexpensive and exhibit improved properties.

52 Claims, 4 Drawing Sheets

OTHER PUBLICATIONS

"Introducing the World-Class Watered Down Idea," a product brochure of Honeycomb Systems, Inc., Biddeford, Me.

"Features of Sontara," a product brochure of E. I. DuPont de Nemours and Company, Wilmington, Del.

"Creative Concepts of Tomorrow's Applications-Kendall Nonwovens," a product brochure of the Kendall Company, Boston, Mass.

CURABLE RESIN COATED SHEETS HAVING REDUCED TACK

RELATED APPLICATIONS

This application is a continuation-in-part of application Ser. No. 047,006, filed May 5, 1987, and also a continuation-in-part of application Ser. No. 784,671, filed Oct. 4, 1985, now U.S. Pat. No. 4,667,661. Both of these parent applications are incorporated herein by reference.

FIELD OF THE INVENTION

This invention relates to sheet materials coated with a curable polymeric resin. More particularly, this invention relates to a curable resin coated sheet material useful in preparing an orthopedic bandage.

BACKGROUND OF THE INVENTION

Current synthetic orthopedic casting tapes are produced using curable resins coated on a substrate (fiberglass, polyester, or other synthetic or natural fabric). U.S. Pat. No. 4,411,262 (von Bonin et al.) and U.S. Pat. No. 4,502,479 (Garwood et al.) disclose the use of water-curable, isocyanate-functional prepolymers in orthopedic casting tapes. After removal of the casting material from the storage pouch, especially after exposure to water used to initiate curing of the prepolymer, these resins are quite tacky until cured. Such tackiness makes it difficult to mold the cast to the patient's limb as the resin tends to stick to the protective gloves worn by the cast applier For example, after the rolls are wrapped but before they harden, some working time is necessary in order to mold the casts to fit the limb. This is accomplished by smoothing the cast with a gloved hand as well as holding the cast at certain points until it hardens. When a roll of tape coated with a tacky resin is used, molding the cast is difficult. The reason for this difficulty is that the glove sticks to the resin, and when attempts are made to smooth the cast and form it, the layers of tape pull apart from each other thus requiring reforming of part of the cast.

It is believed that all curable resin coated orthopedic casting materials currently available commercially suffer from the above-noted problems.

U.S. Pat. No. 3,089,486 (Pike) discloses the use of beeswax as a release agent in the formation of an immobilizing orthopedic structure reinforced with a methacrylate polymer.

U.S. Pat. No. 4,100,122 (Kent) discloses the addition of crystalline wax to a mixture of transpolyisoprene and glass fibers to improve the flow characteristics of the composition during preparation, and the use of such compositions in moldable orthopedic devices.

U.S. Pat. No. 3,043,298 (Brickman et al.) discloses the addition of hydroxypropylmethyl-cellulose to a plaster of Paris bandage to be used as an orthopedic cast which gives the plaster of Paris a creamy consistency or texture when wet with water just prior to application.

U.S. Pat. No. 3,763,858 (Buese) discloses a composite material, useful as a surgical, medical, or orthopedic wrapping, which will adhere or cohere to another surface or to itself by the application of moderate pressure either at room temperature or at an elevated temperature and will be substantially nontacky to the touch until the application of such moderate pressure. The composite material comprises a cementitious core having bonded thereto a flexible, open cellular, resilient polymeric protective covering, the core having sufficient softness at the conditions of use to extend through the cells of the protective covering and become available at the outer surface thereof upon application of moderate pressure.

U.S. Pat. No. 3,630,194 (Boardman) discloses an orthopedic bandage comprising a flexible carrier supporting a solid water-soluble vinyl monomer selected from the group consisting of diacetone acrylamide and an isopropyl diacrylamide and mixtures thereof. The bandage is prepared for use by dipping in water in the presence of a catalyst for initiating polymerization of the vinyl monomer and then wrapping the body portion to be immobilized. The patent also discloses the use of inorganic fillers such as calcium sulfate, calcium carbonate, bentonite, or silica, to render the bandage less sticky and moderate any temperature rise during curing.

U.S. Pat. No. 4,454,873 (Laufenburg et al.) discloses an orthopedic cast material having a thermoplastic material and a quantity of polyethylene oxide applied thereto as an anti-block agent to prevent adherence of adjacent convolutions of the cast material when it is in the form of a roll and is immersed in hot water prior to being wrapped on a limb or body part of a patient. The polyethylene oxide can be in the form of a coating on the outer surface of the cast material or in the resin of the cast material. The patent implies that most, if not all of the polyethylene oxide is removed from the casting material when the casting material is removed from the hot water and that talc can be added to the resin to reduce tack.

U.K. Patent Application No. 2,092,606 (Potter et al.) discloses water hardenable splinting bandages comprising a flexible fabric carrying an isocyanate terminated prepolymer having a reaction functionality of two and a catalyst, which bandage is characterized in that the prepolymer is a water absorbing isocyanate terminated prepolymer and the catalyst is water soluble but insoluble in the prepolymer, wherein the prepolymer is derived from an ethylene oxide adduct. The application discloses that the catalyst is preferably an inorganic material which has an alkaline reaction in water, preferably a carbonate or bicarbonate.

A glove lubricant comprised of water, sorbitol, mineral oil and silicone fluid has been sold by 3M Co., St. Paul, Minn. under the tradename Cast Cream with instructions to apply the lubricant to the gloves of one applying an isocyanate-functional prepolymer coated cast after wrapping of the cast but before molding of the cast to avoid having the exposed casting material adhere to the gloves of the one applying the east.

Thus, the tackiness of prior art resin impregnated materials has caused significant application problems in the orthopedic art. In view of the foregoing, it would be a significant advancement in the art to provide resin impregnated materials which can be used in orthopedic applications, wherein the resin employed exhibits a relatively tack-free surface, thereby greatly facilitating application of the materials. Such resin impregnated materials and methods for applying the same are disclosed and claimed herein.

SUMMARY OF THE INVENTION

This invention relates to an article comprising a prelubricated curable resin-coated sheet surface of the sheet material exhibits a kinetic coefficient of friction of less than about 1.2. The article may be prepared by providing a lubricant at a major surface of the coated sheet wherein said lubricant is comprised of:

(a) hydrophilic groups which are covalently bonded to the curable resin, or (b) an additive which is incompatible with the curable resin, or (c) a combination of (a) and (b);

and wherein said lubricant is present in an amount such that the kinetic coefficient of friction of the sheet material is less than about 1.2. The additive lubricants are preferably selected from the group consisting of:

(i) a surfactant, (ii) a polymer comprised of a plurality of hydrophilic groups, (iii) a polysiloxane, and (iv) mixtures of any of (i), (ii) and (iii).

As discussed hereinafter, the tack exhibited by a surface of a sheet correlates with the kinetic coefficient of friction of the surface such that a reduction in the tack results in reduction of the kinetic coefficient of friction.

This invention also relates to methods of preparing the article described above. More particularly, this invention relates to a method of reducing the tack of a surface of a curable resin coated sheet comprising depositing a layer of a lubricating composition comprised of an additive which is incompatible with the curable resin onto one or more major surfaces of a sheet coated with a curable resin wherein the lubricating composition is present in an amount sufficient to reduce the kinetic coefficient of friction of the major surfaces of the sheet to less than about 1.2 and wherein said layer is deposited before said sheet is wrapped about a substrate. The layer may be deposited onto the surface of the sheet by spraying, by roll coating, or by dipping the sheet into a composition containing the lubricant, e.g., the lubricants that are compatible with water can be added to the water in which the sheet is dipped to effect cure.

This invention also relates to a method of preparing a sheet coated with a curable resin and having reduced tack comprised of coating a sheet with a mixture comprised of:

(a) a curable resin; and (b) an additive which is incompatible with the curable liquid resin;

wherein the amount of the additive is sufficient to reduce the kinetic coefficient of friction of the major surfaces of the sheet to less than about 1.2.

This invention also relates to a method of preparing a sheet coated with a curable resin and having reduced tack comprised of coating a sheet with a curable resin wherein the curable liquid resin is comprised of hydrophilic groups which are covalently bonded thereto and which are present in an amount sufficient to reduce the kinetic coefficient of friction of the major surfaces of the sheet material to less than about 1.2.

The pre-lubricated sheet of this invention exhibits reduced tack prior to and/or during cure of the prepolymer, and yet can be wrapped upon itself to form a laminate comprising adjacent layers of material with the resultant laminate exhibiting acceptable strength and lamination of the wrapped layers. As used herein, a pre-lubricated sheet is a sheet which has the lubricant at the surface of the coated sheet prior to wrapping of the sheet about a substrate, including when used as an orthopedic support material.

DETAILED DESCRIPTION OF THE INVENTION

The embodiments of this invention may be classified into one or more of three classes. In one class, a lubricant is an additive which is chemically unreactive with the curable resin, e.g., a polydialkylsiloxane or an alkyl ionic surfactant as described below. In a second class, the additive is reactive with the resin such that at least a portion of the amount of lubricant may become chemically bonded to the resin, e.g., a hydroxyl-functional surfactant. In a third class, the lubricant is comprised of hydrophilic groups covalently bonded to the resin. Further, these classes are not mutually exclusive in that a single embodiment of this invention may be comprised of a lubricant from all three classes, i.e., a combined lubricant. Indeed, the best mode of this invention is a combined lubricant.

The reactive lubricant additives will vary in the degree to which they react with the resin based on (1) their inherent reactivity, e.g., primary hydroxyl additive lubricants may react faster than secondary hydroxyl lubricants, (2) the length of the period of time from the addition of the reactive additive to the initiation of curing by exposure to water, e.g., the longer the period, the greater the amount of reactive lubricant which will have reacted with the prepolymer to become chemically bonded thereto, and (3) in the case of reactive lubricant additives which are deposited on a curable resin coated sheet the greater the rate of mixing of the reactive lubricant and the curable resin, the greater the amount of lubricant reacted with the resin.

Because of these various factors, it is not convenient to determine precisely to what extent a given reactive lubricant additive applied in a given manner at a given time is chemically bonded to the resin. Accordingly, the disclosure below will not deal with the question of the extent to which a reactive lubricant additive may, in fact, be chemically bonded to the resin. Moreover, because the determination of the extent to which a given reactive lubricant additive is chemically bonded to the resin is unnecessary insofar as the utility of the lubricant in reducing tack is concerned, no distinction will be made below between unreactive and reactive lubricant additives, i.e., the unreactive and reactive lubricant additives will be disclosed together in Section II, below, apart from the bound lubricants disclosed in Section I, below.

The embodiments of the invention which employ a polysiloxane as a lubricant exhibit reduced tack both prior to and after exposure of the prepolymer to water.

The kinetic coefficient of friction of the articles of this invention generally range from about 0.2 to about 1.2, more preferably less than about 0.75 and most preferably less than about 0.4.

One element of this invention is a semi-rigid or flexible sheet upon which a curable resin can be coated or impregnated to reinforce the sheet when the resin is cured thereon. The sheet is preferably porous such that at least a portion of the sheet, and preferably most of the sheet, is impregnated with the resin. As used herein, the term "impregnated" means thoroughly intermingled with the physical structure of the sheet. The resultant resin impregnated sheet is also preferably flexible enough to conform to irregular surfaces.

Examples of suitable sheets are nonwoven, woven, or knit fabrics comprised of natural or synthetic fibers. Preferred sheets include knit fiberglass fabrics, and particularly preferred sheets of this type are extensible, heat-set fabrics as disclosed in U.S. Pat. No. 4,609,578, which issued Sept. 2, 1986. However, as discussed in more detail hereinafter, certain nonwoven fabrics are also presently preferred. If desired, the edges of the sheet may be joined such that a tubular or cylindrical sheet is provided.

The curable resins useful in this invention are resins which can be used to coat a sheet material and which can then be cured to reinforce the sheet material. Preferred resins are those cured with water. A number of classes of water curable resins known in the art are suitable, including polyurethanes, cyanoacrylate esters, and, when combined with moisture sensitive catalysts, epoxy resins and prepolymers terminated at their ends with trialkoxy-silane or trihalo-silane groups. However, resin systems other than those which are water curable may also be used.

I. BOUND LUBRICANTS

One aspect of this invention is a sheet, e.g., a scrim, coated with a curable resin wherein one or more hydrophilic groups are chemically bound to the resin. When this orthopedic casting material is brought into contact with water, the hydrophilic group causes the resin to become slippery. This allows for easy application and molding of the cast for the most efficacious fit without the casting material sticking to the gloved hands of the person applying the cast. As noted above, this is advantageous because if the casting material is sticky, application and molding of the cast is difficult. Further, because the hydrophilic groups are chemically bonded to the curable resin, they cannot be leached out by contact with water subsequent to curing. Accordingly, any potential for skin irritation is reduced.

The curable resin containing bound hydrophilic groups can be prepared by a variety of methods. One method relates to the introduction of hydrophilic groups into a curable resin. For example, an aromatic isocyanate-functional prepolymer can be sulfonated with sulfuric acid or its derivatives or with derivatives of sulfonic acid to obtain a sulfonated isocyanate-functional prepolymer.

A second method relates to the polymerization of monomers comprised of hydrophilic groups to form a curable resin. For example, the preferred resin is an isocyanate-functional prepolymer that is, at least in part, the reaction product of an active hydrogen compound or oligomer with an isocyanate-functional compound or oligomer wherein at least one of the reactants is comprised of at least one hydrophilic group such that the reaction product retains sufficient hydrophilicity to give the prepolymer the desired kinetic coefficient of friction when contacted with water. Preferred prepolymers are prepared from hydroxyl-functional oligomers comprised of hydrophilic groups having repeating units derived from ethylene oxide Many hydrophilic functional group prepolymers are suitable for making moldable orthopedic casting materials within the scope of this invention. Preferred isocyanate-functional prepolymers are prepared by reacting a polyisocyanate compound or oligomer, e.g., diphenylmethanediisocyanate, (MDI), with an active hydrogen compound or oligomer comprised of groups selected from the following:

(1) alkali metal salts of sulfated or sulfonated polyesters or polyethers, (2) quaternary ammonium salts containing carbamates derived from polyesters or polyethers, (3) alkali metal salts of phosphonated or phosphated polyesters or polyethers, and (4) polyethylene oxide.

The curing of an isocyanate-functional prepolymer coated sheet is generally initiated by immersion of the sheet in water. Accordingly, the hydrophilicity of the water-curable isocyanate-functional prepolymer should not be so great that the resin composition is very dispersible in water which would allow the resin composition to leach out into the water bath in which the sheet is immersed. Therefore the hydrophilicity of the prepolymer should be such that the prepolymer is not appreciably dispersible, if at all, in water at ambient temperatures. By not appreciably dispersible, it is meant that a roll of curable resin coated sheet when immersed in water and squeezed several times while immersed will retain at least about 70%, more preferably at least about 85%, and most preferably at least about 95% by weight of the resin composition on the sheet. Further, water retained in or absorbed into the cured resin may adversely affect the rigidity of the cured resin and thereby reduce its wet strength. Accordingly, the hydrophilic functionality of the cured resin should be controlled such that excess amounts of water are not retained in, or absorbed into the cured resin. The hydrophilicity of the resin composition can be controlled by choosing prepolymer-forming reactants having sufficiently low hydrophilic group functionality that the reactants are not appreciably dispersible in water or by using amounts of dispersible reactants that are minor compared to the amounts of reactants that are not appreciably dispersible in water. For example, when the prepolymer is prepared from a mixture of an aromatic isocyanate, e.g., 2,2-diphenylmethane diisocyanate (MDI) and one or more polyether polyols having only polyethylene oxide as a hydrophilic group, the amount of polyethylene oxide by weight of the prepolymer resin should be less than about 15 percent, preferably less than about 10 percent, most preferably less than 6 percent, e.g., 3–4 percent.

EXAMPLEs 1–6 illustrate embodiments of bound lubricants.

II. ADDITIVE LUBRICANTS

In another aspect of this invention, the lubricant is an additive. The additive is incompatible with the curable resin such that the additive forms a shear layer on the surface of the curable resin. Accordingly, the term "incompatible" as used herein shall mean the ability of any composition to form a shear layer on the surface of a curable resin. In most instances, this requires that the additive be at least partially insoluble in the curable resin. Some additives, e.g., the ionic alkyl surfactants form a shear layer when wetted with water. These additives can be mixed with the resin before application of the resin to the sheet (and subsequently allowed to separate from the resin), but are preferably deposited directly on the surfaces of a curable resin coated sheet in an amount sufficient to reduce the kinetic coefficient of friction of the coated sheet during cure.

The additive is deposited on the surface of the casting material prior to wrapping about a substrate in any manner which will deposit the amount necessary to reduce the kinetic coefficient of friction to the desired level. The additive is preferably coated on the surfaces of the casting material prior to the packaging thereof, but it may be applied just prior to the wrapping of the casting material. In particular, some additives may be added to a water bath in which the casting material may be immersed to activate the curing of the prepolymer in an amount sufficient to deposit the desired amount of lubricant on the surfaces of the casting material.

The additive lubricants will be discussed hereinbelow as follows:
A. Polysiloxanes
B. Surfactants and Polymers Consisting of Hydrophilic Groups
　　1. Ionic Alkyl, Aryl, Aralkyl Surfactants
　　2. Polyethoxylated Surfactants
　　　a. Polyethoxylated Alcohols
　　　b. Block Copolymers of Propylene Oxide and Ethylene Oxide
　　3. Ionic Derivatives of Polyethoxylated Alcohols.

Polysiloxanes

Two classes of hydrophobic materials were initially evaluated as lubricants: organic based oils and waxes and silicone based fluids. Of those materials evaluated only those compounds which are essentially immiscible with the resin maintained a lubricating feel after being stored for longer than a few days. Materials such as corn oil; mineral oil; and hydrocarbons such as hexadecane and motor oil did give a non-tacky and even slippery feeling surface which allowed easy application and moldability of the casting tape to the patient, but the effect was transient. On the average, the slippery effect induced by these materials lasted only a day to a week apparently due to dissolution of the lubricant into the resin. Compounds such as lanolin, when applied to the surface of the coated tape in the molten state did remain on the surface of the resin for an extended period of time and did reduce the tackiness of the resin. but also affected the cast detrimentally by reducing the lamination of the casting material.

Unlike the materials discussed above, the silicone based fluids dramatically reduced the tackiness of the resin and surprisingly did not affect the other properties of the cast and even at elevated temperatures remained on the surface of the resin and remained slippery Accordingly, this aspect of the invention relates to the use of lubricating silicone fluids which are generally non-irritating to skin in order to reduce the tackiness of curable liquid resin coated casting tapes The fluids are preferably applied to both major surfaces at 0.9–9.0 g/m² resulting in a casting tape which is easy to apply and mold to a patient's limb. The silicone fluids in the amounts stated above do not adversely affect the physical properties of the cast, and many are safe for use on the skin.

Specifically, the use of the following silicone based compounds is contemplated:

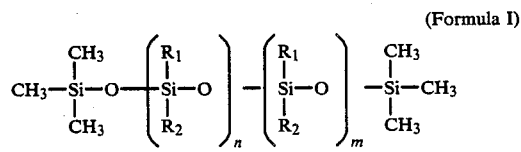

(Formula I)

$R_1$ and $R_2$ may independently be: alkyl ($C_1$–$C_{16}$) chosen independently from: optionally substituted alkyl, optionally substituted aryl, optionally substituted aralkyl, unsaturated alkyl, alkoxy, provided that $R_1$ and $R_2$ are of short enough chain length relative to n and to prevent dissolution of the silicone compound in the resin, m and n are integers, the sum of which range from about 15–800. This value depends on the exact nature of $R_1$ and $R_2$ and the range given is reflective of current commercially available compounds.

Alternatively, the polysiloxane may be terminated with a nonsiloxane moiety. Such polysiloxanes have the following structure:

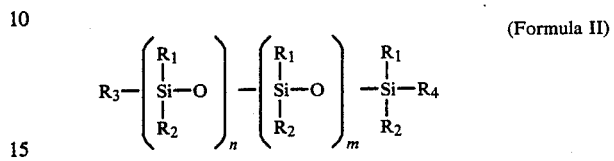

(Formula II)

where $R_1$ and $R_2$ are as given above, preferably methyl $R_3$, $R_4$ may be chosen from: aminoalkyl dimethylsilyl, hydroxyalkyl dimethylsilyl, polyethylene oxide dimethylsilyl, carboxyalkyl dimethylsilyl, chloromethyl dimethylsilyl, methacryloxyalkyl dimethylsilyl, and m and n are integers, the sum of which is such that the viscosity is in the range of 50–10,000 centipoise (cs).

This value is reflective of the presently available compounds.

Finally, the polysiloxane may also be of a tertiary structure as follows:

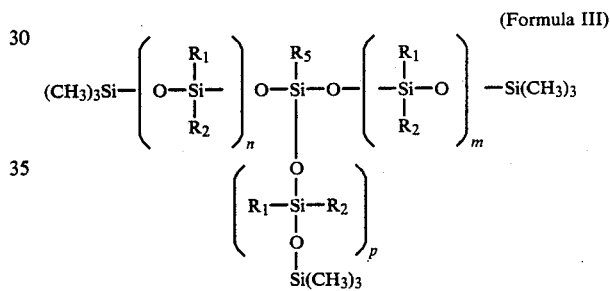

(Formula III)

where $R_1$, $R_2$ are as given above, preferably methyl, and $R_5$ may be chosen from: optionally substituted alkyl, optionally substituted aryl, and optionally substituted aralkyl. It should also be noted that tertiary siloxane structures such as this could also be terminated in nonsiloxane moieties; m, n and p are integers the sum of which is sufficient such that the viscosity is in the range of 25–10,000 cs.

Some examples of the modified silicones described above include: Aminopropyldimethyl terminated polydimethylsiloxanes, ethylene-dimethylsiloxane oxide ABA block copolymers (approximately 1–20% polyoxyethylene), dimethylsiloxane-vinylmethYl siloxane copolymers, tertiary structured polydimethylsiloxanes with phenethylsulfonate or carboxypropyl functionalities at the branch points, methyldecylaryloxymethylsiloxane copolymers, polymethyl-3,3,3-trifluoropropylsiloxane, dimethyldiphenylsiloxane copolymers, poly(acetoxypropyl)methylsiloxane , polybis(cyanopropyl)siloxane , polydiethoxysiloxane, polydiethylsiloxane, and poly(chlorophenyl)-methylsiloxane The preferred polysiloxanes are commercially available polydimethylsiloxanes of viscosities ranging from 50–500 centistokes (cs) which are applied to the casting tape at 0.9 to 9.0 g/m², preferably 1.8 to 5.4 g/m : of casting tape. The higher viscosity fluids up to 350 cs tend to require less material per unit length of tape in order to achieve the desired slippery feel. No significant advantage is apparent in increasing the viscosity from 350 to 500 cs. To these fluids have also been added both ionic and nonionic surfactants. In all cases, casting tape which exhibited reduced tack and dramatically improved moldability resulted with no adverse effect on strength or lamination of the cast.

Ionic and non-ionic surfactants can be added to the silicone fluids in order to further reduce the kinetic coefficient of friction when wet. These include dioctylsulfosuccinate (Aerosol OT), nonionic polyethoxylated room temperature waxy surfactants such as Brij ™, Tergitol ™, Ethosperse ™, Generol ™, and Pluronic ™. In addition, polymeric and clay-type water activated materials have also been added to the silicone fluids to enhance the slippery feel of the casting tape. These materials include polyacrylamides, bentonite, and Keloloid ™ O.

Examples of the polysiloxane embodiments of this invention are shown in Examples 7–14.

Surfactants and Polymers Comprised of Hydrophilic Groups

Another aspect of this invention is a modification of the casting tape used in orthopedic casts in which the coated rolls of tape are rendered non-tacky after immersion in water by the addition of surfactants or polymers comprised of hydrophilic functional groups to the composition.

As has been suggested, a variety of polymeric materials consisting essentially of hydrophilic groups are suitable for use as lubricants. Examples of such polymers include, but are not limited to water soluble polymers based on ethylenically unsaturated monomers such as acrylamide, vinylpyrrolidone, vinylacetate and its polymeric hydrolyzed derivatives, hydroxy and amino functional lower alkyl acrylates such as 2-hydroxyethyl acrylate and various specialty monomers containing ionic species.

The preferred surfactants and polymers comprised of hydrophilic groups are discussed in Sections 1–3 below.

1. Ionic Alkyl, Aryl or Aralkyl Surfactants

This aspect of the invention relates to the use of particular lubricants added to polymers used on orthopedic casting tapes which render them non-tacky. In these embodiments, the lubricant consists of ionic alkyl, ionic aryl, or ionic aralkyl compounds. The alkyl compounds generally contain more than about eight contiguous methylene units per molecule which give the compound fatty characteristics. The ionic alkyl compounds can be anionic, cationic or zwitterionic in nature, for example, sodium hexadecyl sulfate and cetyl trimethyl ammonium bromide and lecithin derivatives. Examples of the aryl and aralkyl ionic compounds are the naphthalene sulfonates and alkylbenzene sulfonates, respectively. In practice, the ionic compounds may be added to the isocyanate-functional prepolymer during formulation generally at a level of from about 1.0% to about 5.0% by weight of the total. The curable resin is coated on a sheet in the standard fashion to give rolls of tape. Alternatively, and preferably, the ionic compound can be deposited on the surface of a curable resin coated sheet.

When immersed in water, the tapes quickly become very slippery. The rolls unwind easily and do not stick to gloves. After the roll is wrapped around the limb, molding of the cast becomes easy due to the non-tacky nature of the resin. The cast can be rubbed over its entire length without sticking to the gloves, and the layers of tape do not separate from each other. This pre-lubricating resin approaches the handling characteristics of plaster of Paris bandages very closely.

In summary, the addition of ionic compound surfactants to an isocyanate-functional prepolymer used in orthopedic casting tapes results in a tape which becomes non-tacky after immersion in water. This is advantageous in that the resulting coating material mimics the properties of a plaster bandage in its ease of application and handling. The rolls unwind easily and molding of the cast is facilitated. Despite its slipperiness, the layers of tape laminate well to each other.

2. Polyoxyethylated Surfactants

This aspect of the invention relates to the use of polyoxyethylated surfactants which, when applied to the surface of curable liquid resin coated casting materials or incorporated into the resin, produce a casting product which is slippery and easy to mold to a patient's limb. These materials are of relatively high molecular weight and are generally waxy at room temperature. In addition, the skin permeability and general toxicity of these materials is very low, making them well suited for addition to an orthopedic bandage. These compounds may be combined with the silicones described above in order to yield a casting material which is non-tacky when dry and very slippery when wet. In addition, these compounds are active as lubricants even when hard water is used to cure the prepolymer.

The following chemical classes of materials when applied to the surface of a casting tape as previously described have been found to yield the desired non-tacky or slippery casting materials.

a. Polyethoxylated Fatty Alcohols

The general structural formula of this class of compounds is represented by the following:

$$R((OCH_2)_nOH)_a \qquad \text{(Formula IV)}$$

wherein
R is a group having a functionality of a and is a saturated or unsaturated alkyl group, optionally halogenated (e.g., chain length $C_8$–$C_{20}$), an aryl group such as an alkylphenyl, or a polyalicylic group (e.g., a sterol derivative);
n is an integer from 3–200, preferably about 20 to about 100; and
a is from 2 to about 10.

The Hydrophile-Lipophile balance (HLB) is greater than 11 and more preferably greater than 15. Examples of these compounds include: Brij ™ series, Tergitol ™ 15-S series, Generol ™ 122E series, Ethosperse ™ series, etc. as described below.

It is believed that only those compounds of this class which are solids at room temperature will be effective in producing a slippery casting material with commercially acceptable shelf life for use as an orthopedic bandage.

b. Block Copolymers of Propylene Oxide and Ethylene Oxide

The general structure of this class of compounds may be represented by the following:

$$H(OCH_2CH_2)_a(OCH_2CH(CH_3))_b(OCH_2CH_2)_cOH \qquad \text{(Formula V)}$$

where:
a and c are independently about 3–150, and
b ranges from 0 to about 150 such that the resulting HLB of the compound is greater than about 11.

It has been found that a high molecular weight polyethylene oxide (available from Union Carbide as Carbowax TM) applied to the surface does yield a non-tacky casting material, however, the material was not as slippery as that of the polymeric materials described in 2 a. and b. above of similar molecular weight.

Many surfactants, detergents, and emulsifiers may be useful as slip agents but are unsuitable for use with an isocyanate-functional prepolymer because they adversely affect the shelf-life of that prepolymer and, more importantly for medical uses, are deleterious to skin. Non-ionic surfactants, especially those of higher molecular weight described herein, are known to have extremely low or nondetectable skin permeability and are often reported as additives to cosmetic and pharmaceutical formulations as a means of reducing skin permeability to detergents and other more toxic substances. The nonionic surfactants of this invention, for the most part, are not skin irritants and usually contain functionalities which allow them to react with the resin, thus minimizing the possibility of direct or prolonged skin contact.

The surfactants useful in this invention are commercially available from many suppliers. The following have been shown to be useful:

ICI Americas Inc.:
  Brij TM 58-20 mole polyoxyethylene cetyl ether,
  Brij TM 78-20 mole polyoxyethylene stearyl ether,
  Brij TM 99-20 mole polyoxyethylene oleyl ether,
  Brij TM 700-100 mole polyoxyethylene stearyl ether;
Glyco Chemicals Inc. (Williamsport Pa.):
  Ethosperse TM CA-20-20 mole polyoxyethylene stearyl ether,
  Pegosperse TM CO-200-200 mole polyoxyethylene castor oil;
Henkel-Specialty Chemicals Div. Teaneck, N.J.:
  Generol TM 122E-16-16 mole polyethylene glycol soya sterol,
  Generol TM 122E-25-25 mole polyethylene glycol soya sterol,
  Eumulgin TM B2-fatty alcohol polyglycol ether;
Union Carbide:
  Tergitol TM 15-S-40-Alkoxy ($C_{12}$–$C_{14}$) polyethyleneoxyethanol avg. molecular weight (M.W.) 1960,
  Tergitol TM NP-40-Nonylphenol polyethylene glycol ether avg. molecular weight 1980;
BASF Wyandote:
  Pluronic TM F-68 Polyethylene oxide terminated polypropylene oxide, 80 mole % EO, avg. M.W.=8350,
  Pluronic TM F108 Polyethylene oxide terminated polypropylene oxide, 80 mole % EO, avg. M.W.=14,500,
  Pluronic TM F127 Polyethylene oxide terminated polypropylene oxide, 70 mole % EO, avg. M.W.=12,5000,
  Pluronic TM P65 Polyethylene oxide terminated polypropylene oxide, 50 mole % EO, avg. M.W.=3400.

Other suppliers are available for these types of surfactants. In order to achieve a non-tacky feel both dry and wet, these surfactants are usually combined with the silicone fluids described above.

3. Ionic Derivatives of Polyethoxylated Alcohols

This aspect of the invention relates to the use of ionic derivatives of polyethoxylated alcohols (IPEA) which when applied to the surface of isocyanate-functional prepolymer casting resins effectively reduce or eliminate the tack without significantly affecting other properties. of the casting material. This effectively increases the ease of application of the casting tape as well as the moldability to the patient's limb. The IPEA class of materials is useful in synthetic casting resins for several reasons IPEA's have very low or no skin permeability and in most cases no skin irritation; many yield little or no foaming; IPEA's are active in hard water (e.g., in water used for plaster casts); and in most cases, the IPEA surfactants are waxy, and therefore, can be applied to the surface of the casting tape in a molten state and subsequently allowed to solidify. This latter property allows the surfactant to remain on the surface of the tape where it is most active and also makes the roll easier to unwind.

Specifically, the following surfactant structures will yield the desired properties:

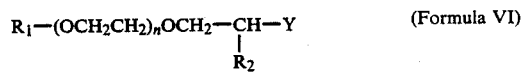
(Formula VI)

where
$R_1$ may be a straight or branched chain hydrocarbon and n is at least 3. The length of the hydrocarbon must be in balance with that of the polyethylene oxide chain to give the ethoxylated nonionic primary alcohol a HLB in the range of 11–35 and more preferably in the range of 15–25. $R_1$ may be selected from saturated or unsaturated optionally halogenated alkyl (preferably $C_1$–$C_{20}$, more preferably $C_8$–$C_{18}$), aryl or optionally substituted aryl, and aralkyl (preferably $C_7$–$C_{24}$).
Y is a derivative of the alcohol and is an organic or inorganic salt of a group selected from —$OSO_3H$, —$SO_3H$, —$OPO_3H$, and —$N(R_1)_3{}^+$.
$R_2$ is hydrogen or is selected from the same group as $R_1$.

It has been found that the IPEA's described herein can either be added directly to the resin at concentrations ranging from 0.5–7% or preferably, applied to the surface of the tape at coating weights of 0.45 to 6.3 g/m² (preferably 0.9 to 3.6 g/m ) The higher melting compounds may be suspended in a carrier fluid such as silicones, organic oils, or suitable solvents in order to be sprayed. Silicone fluids or nonionic polyethoxylated waxes, such as those described above, may be used in conjunction with the IPEA in order to augment the slippery feel. Furthermore, it is possible that other surfactants which may be more skin irritating than some of those of the IPEA may be added in reduced amounts in order to increase the slipperiness of the casting material without compromising the skin biocompatibility. In addition, bactericidal surfactants may also be added in order to effectively kill ba oteria between the skin and cast for better hygiene (e.g., benzalkonium chloride or Cetrimide B.P.).

IPEA type surfactants are commercially available from several chemical suppliers including Shell Chemical (Neodol TM 3S and 3A), Henkel TM (Standopol series), and DuPont Zonyl TM UR (polyfluoroaliphatic ethoxylated phosphonate).

III. COMBINED LUBRICANTS

As noted above, the lubricant may be comprised of both hydrophilic groups bound to the prepolymer and one or more additive lubricants. The particular procedures used in obtaining a bound lubricant and the particular procedures used with additive lubricants are used in conjunction with one another, generally without modification. For example, a casting tape coated with a curable liquid resin having bound hydrophilic groups in accordance with Example 1 below can be coated with a polysiloxane lubricant in accordance with Examples 6–13, to obtain an article in accordance with this invention, as in Example 23.

One advantage of the combined lubricants resides in the pre-wetted reduction in tack provided by a polysiloxane and the great reduction in tack provided by a bound lubricant after initiation of cure by exposure to water.

Test for Determining the Coefficient of Friction of Synthetic Casting Tapes

Determination of the frictional properties of many materials is often measured in terms of the coefficient of friction. This type of measurement may be made when sliding the material of interest over itself or over another object. The coefficient of friction is a dimensionless term which quantifies the frictional properties and may distinguish between surfaces of varying roughness, tackiness, slipperiness, etc. In the present application, a wide variety of lubricating properties are generated by surfactants or other surface active materials which are either added directly to the casting resins prior to coating the scrim, or applied to precoated tape. A test has been developed which measures the tack, i.e., kinetic coefficient of friction of these various materials. This test method is based on ASTM test method D 1894 ("Static and Kinetic Coefficients of Friction of Plastic Film and Sheeting") and measures the kinetic coefficient of friction between a horizontal stationary piece of test specimen in low tension and a 200 g 304 stainless steel sled polished to a No. 4 finish. The procedure and apparatus of ASTM test method D 1894 have been modified to accommodate relatively rough and elastic materials such as synthetic casting tapes. This method yields empirical data which, for the most part, correlates with actual performance and thereby offers a quantitative measurement of the lubricating properties of a given casting material.

As used herein, the following terms have the following meanings:

"Kinetic Friction"—the resisting or opposing force that arises when a surface of one object slides over the surface of another object.

"Kinetic Coefficient of Friction"—(KCOF) the ratio of the kinetic frictional force to the force acting perpendicularly to the two surfaces in contact (usually the gravitational force). This dimensionless term is a measure of the relative difficulty with which the two materials will slide across one another i.e., the higher the coefficient of friction, the more difficult it is to slide the two materials over one another. The kinetic coefficient of friction, as used herein, is determined from the test described hereinafter and is calculated by the equation:

$$\text{Kinetic Coefficient of Friction} = \frac{\text{force required to pull the sled (g)}}{200 \text{ (g)}}$$

Test Method

SAMPLE AND MATERIALS CONDITIONING

Sample Conditioning—Test samples should be conditioned at 21°–25° C. for not less than 24 hours prior to testing.

Water Conditioning—Water for use in this test should be deionized or soft water conditioned to 22°–24° C. Fresh water should be used for each set of samples, i.e., for each lot of test samples.

Test Conditions—Testing must be conducted in a controlled temperature and humidity environment of 21°–25° C. and 45–55% relative humidity.

APPARATUS

A. Sled—A 304 stainless steel half round cylinder 4.92 cm (1 15/16") diameter by 2.54 cm (1.000") wide and 2.54 cm (1.000") high with a 4–40 0.5" thread in one end into which an Instron part no. T53-5 eye screw is fastened. Material is added or removed from the top of the sled so a to adjust the weight to 200±0.5 g. The radiused face of the sled is polished to a No. 4 finish.

Test Fixture—The Instron Coefficient of Friction Fixture (Catalog No. 2810-005) was modified to accommodate testing of casting materials. Specifically, the pulley assembly was raised 2.54 cm (1.000") and an additional Teflon ™ coated brass tension pulley 0.953 cm (0.375") in diameter × 13.34 cm (5.25") was fixed to the end of the table opposite the load pulley and positioned such that the top of the pulley was in the plane of the table. In addition, a 12.7 cm (5")×0.953 cm (0.375")×0.953 cm (0.375") hold down clamp was positioned 7.62 cm (3.0") from the load pulley in order to fix the test specimen in place. A series of weights fixed to spring clamps were fabricated in order to keep the test specimen in tension. The proper weight is determined by the width of the test sample, 0.045 kg/cm (¼ lb/inch) (e.g., with a 7.62 cm (3") wide test specimen a 1.65 kg (¾ lb) weight should be used).

C. Force Measuring Device—An Instron Model No. 1122 Table top measuring instrument equipped with a 50 lb. load cell (Instron assembly No. A-30-39) and connected to an Instron Microcon II microprocessor Model No. MC4100.

PREPARATION OF APPARATUS

1. Assemble the apparatus as described above.
2. Set the drive speed of the sled (i.e., the crosshead speed) to 127 cm (50 inches)/min.
3. Calibrate the 50 lb. load cell using a 500 g weight.
4. The following settings on the control panel of the Instron Model No. 1122 measuring device should be set:

crosshead speed = 127 cm (50 in)/min
full scale load = 0–500 g
cart speed = 12.7 cm (5 in)/min auto
load cell filter = in
polarity = up The Micron II microprocessor should be set to the following:
area = 0
gage length = 2.54 cm (1.10 inch)
speed = 127 cm (50 in)/min
fail criteria = 100%
load limit = 45,360 K grams force
elongation = 100%
crosshead stop = off elongation correction factor = no correction 5. Set up the Microcon II microprocessor Model No. MC4100 to integrate the tension force for travel between 1.27 cm and 19.0 cm (0.5 and 7.5 inches) and to calculate the average tension force. Be sure the first 1.27 cm (0.5") of travel is not included in this calculation to avoid incorporating the static frictional force.

PROCEDURE

The following procedure is appropriate for water-activated casting materials which set, i.e., resist passive motion in about three to five minutes. The water immersion time and subsequent waiting time to initiation of sled movement may require adjustment if the set time of the material to be tested is substantially different from three to five minutes. This procedure is also used to determine the coefficient of friction of dry material by eliminating the water immersion and subsequent waiting time.

1. Open the pouch containing the test specimen, immediately cut the sample to obtain a length of from 46 cm to 61 cm (18 in. to 24 in.) and immediately immerse the sample into 3.8 liter (1 gallon) of fresh 22–24° C tap water without agitation of any kind. Start a stopwatch immersion in the water.

2. After 15 seconds gently remove the test specimen (avoid any agitation) from the water and briskly shake the specimen twice to remove excess water.

3. While avoiding contact with the specimen as much as possible, place the sample flat on the testing table and fix one end into the hold down clamp and attach the proper weight (0.045 kg/cm width or ¼ lb/inch width of tape) to the free end.

4. 15 seconds after the specimen has been removed from the water, gently place the sled on the specimen such that the wire is straight without sagging and under 10–15 g tension.

5. Exactly 3 seconds after the sled has been placed on the specimen, start the driving mechanism which was previously adjusted to a crosshead speed of 127 cm (50 inches)/min.

6. Record the average tension force calculated by the Microcon II microprocessor.

7. Remove the sled and immediately clean the polished sliding surface with a soft paper towel and a solution of 50% acetone and 50% ethanol. Allow the sled to dry.

8. Remove the test specimen, dry and clean off the table, tension pulley, and clamp. If necessary use the cleaning solution of step 7.

EXAMPLES 1–6

Bound Lubricants

EXAMPLE 1

A 3.8 liter (one gallon) glass vessel equipped with a 12.7 cm×2.54 cm×0.318 cm (5×1×⅛") Teflon TM impeller, addition funnel, nitrogen purge line, and thermometer was assembled and purged with nitrogen for 30 minutes to ensure the entire apparatus was completely dry. The following chemicals were added to the reactor through the addition funnel in order and at 5 minute intervals:

| Chemical | Wt (g) | Wt % |
|---|---|---|
| Isonate 143L (Upjohn Co.) | 2151.7 | 58.15 |

-continued

| Chemical | Wt (g) | Wt % |
|---|---|---|
| Benzoyl chloride | 2.59 | 0.07 |
| Pluronic F-108 (BASF) | 148.0 | 4.00 |
| DB-100 (Dow Chemical) | 6.66 | 0.18 |
| Butylated hydroxy toluene (BHT) | 17.76 | 0.48 |
| PPG-425 (Union Carbide) | 217.45 | 5.88 |
| PPG-725 (Union Carbide) | 1109.56 | 29.99 |
| MEMPE (4-[2-[1-methyl-2-(4-morpholinyl)-ethoxy]ethyl]-morpholine | 46.25 | 1.25 |

The agitation rate was gradually increased as the viscosity increased. The vessel was temporarily insulated with glass wool and the temperature of the reaction was allowed to increase (due to reaction exotherm) to 55° C. The glass wool was removed along with the agitator, thermometer, and addition funnel. The vessel was sealed and the resin was allowed to cool for 24 hours.

The resin was coated onto three inch wide knit fiberglass scrim as described in U.S. Ser. No. 668,881, filed Nov.6, 1984, at a resin content of 42.5% by weight. The coated fabric was converted to individual rolls 3.66 m (12 feet) in length. These rolls were packaged individually into moisture proof pouches. Ten days after coating, two of the rolls were unpackaged in a 2% relative humidity environment and cut to 61 cm (24 inch) lengths and resealed individually in the moisture-proof pouches.

Each 60.96 cm (24") sample was then tested according to the KCOF method described above. The samples were found to have a mean kinetic coefficient of friction of 0.29.

EXAMPLE 2

The following resin was prepared, coated and packaged according to the procedure of Example 1:

| Chemical | Wt (g) | Wt % |
|---|---|---|
| Isonate TM 143 L (Upjohn Co.) | 2183 | 59.0 |
| Benzoyl Chloride | 2.6 | .07 |
| Brij TM 700 (ICI Americas Inc.) | 148.0 | 4.0 |
| DB-100 (Dow Chemical) | 6.7 | .18 |
| BHT | 17.8 | .48 |
| PPG-425 (Union Carbide) | 270.1 | 7.3 |
| PPG-725 (Union Carbide) | 1016.4 | 27.5 |
| MEMPE | 55.5 | 1.5 |

Note: Brij 700 is a polyoxyethylene (avg. mol. wt. 100) stearyl ether

This material was tested according to the KCOF method and exhibited a mean kinetic coefficient of friction of 0.28.

EXAMPLE 3

The following resin was prepared, coated and packaged according to the procedure of Example 1:

| Chemical | Wt (g) | Wt % |
|---|---|---|
| Isonate 143L | 2045 | 58.4 |
| Benzoyl Chloride | 2.5 | .07 |
| PEG 8000 | 157.5 | 4.5 |
| DB-100 | 6.3 | .18 |
| BHT | 16.8 | .48 |
| PPG-425 | 280.9 | 8.0 |
| PPG-725 | 947.1 | 27.1 |

| Chemical | Wt (g) | Wt % |
|---|---|---|
| MEMPE | 43.75 | 1.25 |

Note:
PEG-8000 is a polyethylene glycol, having a 20 molecular weight of appox. 8000.

This material was tested according to the KCOF method and exhibited a mean kinetic coefficient of friction of 0.27.

EXAMPLE 4

A hydrophilic oligomeric diol was prepared by reacting dried polyethylene oxide glycol (available from Union Carbide as Carbowax TM 1000) with dried dimethyl sodium sulfoisophthalate in a 4:1 molar ratio at about 220°–250° C. in the presence of a catalytic amount of zinc acetate. This diol, in an amount of 15,164 g, was combined with 1920 grams of trimethylol propane and the mixture was dried by azeotroping with toluene. This was then charged directly into a nitrogen purged vessel containing 26,559 grams of Isonate 143L, 218 g of BHT and 25 g of ethanesulfonic acid. After mixing for about 2 hours at about 60°–80° C., the product was transferred to several 3.785 liter (one gallon) glass jars and sealed under a nitrogen blanket.

One jar containing 4222 grams of the above sulfonated urethane resin was heated at 65° C (150° F.) for about two hours and then 42 grams of 2,2,'-dimorpholinodiethyl ether were mixed in. In a dry room with the humidity held at about 2% relative humidity, the resin was then coated onto three inch wide knit fiberglass scrim as previously described at a resin content of 39.9% by weight. The coated scrim was converted to twelve foot lengths by rerolling onto polyethylene cores and cutting to length. These rolls were packaged individually in moisture-proof pouches.

Five months after coating, the samples were tested according to the KCOF method. These samples were found to have a mean kinetic coefficient of friction of 0.46.

EXAMPLE 5

About one month after coating the scrim in Example 4, several rolls of this material were sprayed on both sides with polydimethylsiloxane 200–100 cs (Dow Corning) at a coating weight of 3.4 g/m in a dry room with the relative humidity held at about 2%. Each length of material was rerolled and sealed in a moisture-proof pouch.

After about 4 months, several samples were tested according to the KCOF method and were found to have an average kinetic coefficient of friction of 0.40. In addition, one sample was tested dry according to the KCOF method, i.e., it was not immersed in water. This sample was found to have a mean kinetic coefficient of friction of 0.32.

EXAMPLE 6

A hydrophilic, oligomeric diol, was prepared by reacting dried polyethylene oxide glycol (Carbowax TM 600) with dried dimethyl sodium sulfoisophthalate in a 2:1 molar. ratio, at 220°–250° C., in the presence of a catalytic amount of zinc acetate. This diol, in the amount of 71.0 grams (0.11 eq.) was combined with 128.0 grams (0.59 eq.) PPG-425 and 49.0 grams (0.10 eq.) PPG-1025. To the stirred mixture, under a nitrogen sweep, were added 3.1 grams BHT, .46 grams benzoyl chloride, 13.3 grams 2,2'-dimorpholinodiethyl ether and 403.0 grams (2.80 eq.) Isonate 143L. The reaction mixture was allowed to exotherm and stirring was continued for 2 hours while the resin cooled.

The resin was coated and packaged according to the procedure of Example 1 except that the resin content was 42% by weight. Samples were tested according to the KCOF method and exhibited a mean coefficient of friction of 0.31.

EXAMPLE 7–14

Polysiloxane Lubricants

In the following Examples, the fluid was sprayed on 7.6 cm (3") casting tape available from 3M as SCPTCHCAST® 2 comprising a knit fiberglass scrim impregnated with an isocyanate-functional prepolymer resin. Spraying was accomplished using either a modified air-brush or a Spraying Systems, Wheaton, IL., atomizing ¼ J spray nozzle unless otherwise indicated. Both sides of the tape were sprayed. The amount of fluid per unit length of tape was controlled by the speed at which the tape was drawn past the sprayer as well as by regulating the flow rate of the spraying apparatus.

EXAMPLE 7

Dow Corning 200-300 cs silicone fluid was sprayed on both surfaces of a casting tape as previously described at a total coating weight of 3.95 g/m². The resulting casting material was very easy to handle both before and after wetting. The sample was then tested according to the KCOF method. The samples exhibited a mean kinetic coefficient of friction of 0.52.

EXAMPLE 8

Dow Corning 200-500 cs silicone fluid was sprayed on both sides of a casting tape as previously described at a coating weight of 3.2 g/m². The mean kinetic COF was 0.62.

EXAMPLE 9

Dow Corning 200-100 cs silicone fluid containing 5% wt/wt Aerosol OT (dioctylsulfosuccinate sodium salt) was sprayed on both sides of a casting tape as previously described at a coating weight of 3.2 g/m². The mean kinetic COF was 0.45.

EXAMPLE 10

Dow Corning 200-50 cs silicone fluid containing 12.3% wt/wt Keloloid O was sprayed on both sides of a casting tape as previously described at a coating weight of 4.3 g/m² roll. The mean kinetic COF was 0.52.

EXAMPLE 11

A tertiary structured polydimethylsiloxane with carboxypropyl groups at the branch points (avail. from Petrarch Systems Inc. as PS-402) was sprayed onto both sides of a casting tape as previously described at a total coating weight of 3.6 g/sq. meter. This material was tested for its lubricating properties according to the procedure of KCOF method and was found to have a mean kinetic coefficient of friction of 0.49.

EXAMPLE 12

A (95-98%) methyldecyl (2-5%) aryloxymethylsiloxane copolymer available from Petrarch Systems Inc. as PS136 was sprayed onto both surfaces of casting tape as previously described at a total coating weight of 3.41 g/sq. meter. This material was tested for its lubricating properties according to the KCOF method and was found to have a mean kinetic coefficient of friction of 0.49.

EXAMPLE 13

A polydimethyl 3,3,3 trifluoropropylsiloxane available from Petrarch Systems as PS181 was sprayed onto both sides of casting tape as previously described at a total coating weight of 2.33 g/sq. meter. This material was tested for its lubricating properties according to the KCOF method and was found to have a mean kinetic coefficient of friction of 0.69.

EXAMPLE 14

A (83–85%) dimethyl (15–17%) diphenylsiloxane vinyl terminated copolymer available from Petrarch Systems, Inc. as PS782 was sprayed onto both sides of casting tape as previously described at a total coating weight of 3.2 g/sq. meter. This material was tested for its lubricating properties according to the KCOF method and was found to have a mean kinetic coefficient of friction of 0.55.

EXAMPLES 15 and 16

Polymers Comprised of Hydrophilic Groups

Cyanomer TM A370 (a polyacrylamide available from American Cyanamide) was coated onto a casting tape, available from 3M as Scotchcast 2 as in Examples 7–14, using a vibratory screen at a coating weight of 4.8 g/m$^2$. The resulting casting tape was tested according to the KCOF method and found to have a mean kinetic coefficient of friction of 0.32.

EXAMPLE 16

A 115,000 molecular weight polyvinyl alcohol available from Aldrich Chemicals, (P.N. 18251-6) was coated described in Examples 7–14, onto casting tape as previous according to the procedure of Example 15, at a coating weight of 4.2 g/m$^2$. The resulting casting tape was tested according to the KCOF method and found to have a mean kinetic coefficient of friction of 0.42.

EXAMPLES 17-27

Surfactant Lubricants

In the following examples the surfactant(s) or surfactant/silicone fluid combination was sprayed, except as noted, on the surface of a casting tape, which tape was previously described in Examples 7–14. An air brush was used to spray on the material. In most cases it was necessary to spray on the material in a hot molten sate in which case the material solidified almost instantaneously upon expansion and exit from the nozzle. Both sides of the casting material were coated with equivalent amounts.

EXAMPLE 17

Casting tape as previously described in Examples 7–14 was evenly coated with Metarin TM P (a 95% phosphatides lecithin composition available from Lucas Meyer Inc., Decatur, Ill.) at a coating weight of 3.6 g/m$^2$. The Metarin P was deposited on the casting tape using a vibratory screen. This resulting casting tape was tested according to the KCOF method and found to have a mean kinetic coefficient of friction of 0.19.

EXAMPLE 18

Sodium dodecyl sulfate was coated onto a casting tape as previously described in Examples 7–14 according to the procedure of Example 15 at a coating weight of 3.6 g/m$^2$. The resulting casting tape was tested according to the KCOF method and found to have a mean kinetic coefficient of friction of 0.23.

EXAMPLE 19

The following resin was prepared, coated and packaged according to the procedure of Example 1 except that the Standopol TM 125E (available from Henkel Corp.) was first dried to remove water.

| Chemical | Wt. (g) | Wt. % |
|---|---|---|
| Isonate TM 143L | 1435.5 | 52.5 |
| Benzoyl Chloride | 1.9 | .07 |
| DMDEE (Texaco) | 77.38 | 2.83 |
| DB-100 | 5.0 | .18 |
| BHT | 12.72 | 0.47 |
| PPG-725 | 1117.5 | 40.9 |
| Standopol TM 125E* | 82.0 | 3.0 |

*(Standpol TM 125E is the sodium sulfonate of a 12 mole ethlene oxide lauryl ether from Henkel Corp.)

This material was tested according to the KCOF method and exhibited a mean kinetic COF of 0.35.

EXAMPLE 20

Generol TM 122E-25 was sprayed on both surfaces of a casting tape at a coating weight of 3.2–3.6 g/m$^2$. The resulting casting material was very slippery when wet. The mean kinetic COF was 0.25.

EXAMPLE 21

Tergitol TM 15-S-40 dispersed in Dow Corning 200–100 cs silicone oil (1:1 w/w) was sprayed on both surfaces of a casting tape at a coating weight of 3.6 g/m$^2$. The product was both non-tacky dry and very slippery when wet. The mean kinetic COF was 0.31.

EXAMPLE 22

Tergitol TM NP-40 was sprayed on both surfaces of a casting tape as previously described in Examples 7–14 at coating weight of 3.6 g/m$^2$. The mean kinetic COF was 0.27.

EXAMPLE 23

Brij 58 TM and Brij TM 78 were sprayed on both surfaces of separate rolls of a casting tape as previously described in Examples 7–14 at coating weights of 3.6 and 53.8 g/m : The mean kinetic COF of each was 0.32 and 0.37, respectively.

EXAMPLE 24

Ethosperse TM CA20 was sprayed on both surfaces of a casting tape as previously described in Examples 7–14 at a total weight of 3.2–2.6 g/sq. meter. The mean kinetic COF was determined to be 0.26.

EXAMPLE 25

Anhydrous Neodol TM 3A (ammonium salt of a 3 mol ethoxylated laureth sulfate) was added in a molten state to hot Dow silicone 200–100 cs fluid to 50% wt/wt, and the resulting mixture was sprayed on both surfaces of a casting tape as previously described in Examples 7-14 at coating weight of 3.6 g/m². The mean kinetic COF was 0.43.

EXAMPLE 26

Anhydrous Standopol ™ 125E (sodium salt of a 12 mole ethoxylated laureth sulfate) was also added in a molten state to hot Dow silicone 200-100 cs fluid to 50% wt/wt,, and the resulting mixture was sprayed on both sides of a casting tape as previously described in Examples 7-14 at coating weight of 2.7-3.2 g/m². The mean kinetic COF was 0.38.

EXAMPLE 27

The following resin formulation was prepared and converted according to the procedure of Example 1. The slip additive, Zonyl ™ UR available from E.I. duPont de Nemours & Co. Wilmington, Del., is a mixture of polyfluoroaliphatic ethoxylated phosphonates having the general structure $((FCH_2CH_2)_{3-8}(OCH_2CH_2)_{1,2}OP(OH)_{2,1})$.

| Chemical | Wt. g | Wt. % |
|---|---|---|
| Isonate ™ 143L (Upjohn) | 1083.3 | 50.8 |
| Benzoyl Chloride | 1.4 | .07 |
| Dimorpholinodiethyl ether (DMDEE) | 58.4 | 2.74 |
| DB-100 (Dow Chemical) | 3.6 | .17 |
| BHT | 9.6 | .45 |
| PPG-725 (Union Carbide) | 843.3 | 39.5 |
| Zonyl ™ UR (DuPont) | 134.4 | 6.3 |

The resulting casting material was tested according to the KCOF method and found to have a mean kinetic COF of 0.93.

Combination Lubricants

EXAMPLE 28

The casting material was produced according to the procedure of Example 1 except that during the converting operation the coated scrim was sprayed with Dow polydimethylsiloxane 200-100 cs. The spraying was done using an air atomizing nozzle at approximately 2.65 g/m² applied to each side of the casting tape. When tested according to the KCOF method, the samples were found to have a mean kinetic coefficient of friction of 0.33.

Comparative Examples A and B packaged according to the procedure of Example 1:

| Chemical | Wt (g) | Wt % |
|---|---|---|
| Isonate ™ 143L (Upjohn Co.) | 2046.10 | 55.30 |
| Benzoyl Chloride | 3.68 | .10 |
| PPG-725 (Union Carbide) | 1582.85 | 43.05 |
| Dimethyl Ethanolamine | 9.28 | .25 |
| Niax ™ A-99 (Union Carbide) | 11.14 | .30 |
| LK-221 (Air Products) | 36.94 | 1.00 |

This material was tested according to the KCOF method and exhibited a mean kinetic COF of 206.

The following resin was prepared, coated and packaged according to the procedure of Example 1:

| Chemical | Wt (g) | Wt % |
|---|---|---|
| Isonate ™ 143L (Upjohn Co.) | 2046.10 | 55.30 |
| Benzoyl Chloride | 3.70 | .10 |
| DB-100 (Dow Chemical) | 37.00 | 1.00 |
| PPG-725 (Union Carbide) | 1592.85 | 43.05 |
| Dimethylethanolamine | 9.25 | .25 |
| Niax ™ A-99 (Union Carbide) | 11.10 | .30 |

This material was tested according to the KCOF method and exhibited a mean kinetic COF of 1.76.

It has been found that the tack of a given isocyanate-functional prepolymer tends to peak during cure. Accordingly, prepolymers which have a longer set time than those exemplified herein, may not exhibit a kinetic COF as high as those of Comparative Examples A and B because cure has not progressed sufficiently at the time specified in the foregoing test procedure. Therefore, the relative rate of cure of prepolymers tested according to the foregoing method should be considered when comparing results of the test for prepolymer systems having variable rates of cure.

EXAMPLE 29

The following example illustrates the advantage and synergism between the use of both a topical silicone treatment and a lubricating agent (Pluronic F108) added to the resin system.

The following resin was prepared and converted according to the procedure of Example 1.

| Chemical | wt.g | wt (%) |
|---|---|---|
| Isonate ™ 143L | 2162.6 | 58.5 |
| Benzoyl Chloride | 2.6 | .07 |
| Pluronic F108 | 148.1 | 4.0 |
| DB-100 | 6.7 | 0.18 |
| BHT | 17.8 | .48 |
| PPG-425 | 270.2 | 7.3 |
| PPG-725 | 1045.9 | 28.3 |
| MEMPE | 46.3 | 1.25 |

The resulting coating material was tested according to the KCOF method with the omission of the water dip (Procedure step 2), i.e., the casting material was tested in a "dry" state. The mean kinetic coefficient of friction was determined to be 2.18.

A casting material prepared according to the procedure above was sprayed with Dow 200-100 centistoke silicone fluid according to the procedure of Example 28. The resulting orthopedic bandage was tested for its lubricating properties in a "dry" state according to the procedure of Example A. The mean kinetic coefficient of friction was found to be 0.80.

The mean kinetic coefficient of friction of the silicone sprayed material wetted in accordance with the KCOF method was 0.33.

EXAMPLE 30

This example sets forth one of the presently most preferred embodiments of the present invention where a bound lubricant is incorporated into a resin coated sheet for orthopedic use. In this example, the following resin was prepared, coated, and packaged according to the procedure of Example 1:

| Chemical | Wt (g) | Wt (%) |
|---|---|---|
| Isonate 143L (Upjohn Co.) | 1975 | 56.4 |
| Benzoyl chloride | 1.75 | 0.05 |
| DB-100 (Dow Chemical) | 6.31 | 0.18 |
| Butylated hydroxy toluene (BHT) | 16.83 | 0.48 |

-continued

| Chemical | Wt (g) | Wt (%) |
|---|---|---|
| PPG-425 (Union Carbide) | 424.4 | 12.1 |
| PPG-725 (Union Carbide) | 888.8 | 25.4 |
| Pluronic F-108 (BASF) | 140.0 | 4.0 |
| MEMPE | 46.2 | 1.32 |

This material was tested according to the KCOF method and exhibited a mean kinetic coefficient of friction of 0.35.

SOME PRESENTLY PREFERRED NONWOVEN SHEET MATERIALS FOR USE WITH THE PRESENT INVENTION

In addition to the particular sheet materials discussed hereinabove, certain nonwoven fabrics have also been found to be useful in producing resin coated sheets having reduced tack within the scope of the present invention. Such nonwoven fabrics are disclosed and claimed in commonly assigned, copending application Ser. No. 047,006, filed May 5, 1987.

Thus, the present invention also relates to orthopedic support materials or coating materials having reduced tack which utilize a nonwoven, stretchable fabric which, when loaded with resin, is easily moldable and permits good palpation of bone structure during application. The nonwoven fabric is preferably made of a relatively inexpensive material, such as a presently preferred nonwoven polyester material. The nonwoven fabric comprises fiber bundles and apertures between the fiber bundles, with each of the fiber bundles comprising a plurality of fibers having interstices therebetween. A curable prepolymer resin (such as an isocyanate functional, polyurethane prepolymer resin) is impregnated into the interstices between the fibers of each fiber bundle so as to impart sufficient strength to the material upon curing to be used as an orthopedic casting material, while leaving the apertures between fiber bundles substantially unoccluded so as to produce a porous finished cast which permits sufficient water vapor permeability therethrough to substantially avoid skin maceration.

Such orthopedic casting materials not only exhibit better moldability and palpability than prior art non-plaster of Paris casting materials, but may also be made to be significantly less expensive than prior art non-plaster of Paris casting materials. The orthopedic casting materials of the present invention preserve the advantages characteristic of non-plaster of Paris materials, and in some instances provide additional advantages. In this regard, the orthopedic casting materials of the present invention have been found to exhibit improved resin holding capacity and other improved properties over prior art non-plaster of Paris orthopedic casting materials.

It is, therefore, an object of the present invention to provide orthopedic casting materials having reduced tack which avoid the use of plaster of Paris, which exhibit good conformability and moldability, and which allow for good tactile manipulation and good palpation of the one structure through the casting materials.

Another object of the present invention is to provide orthopedic casting materials having reduced tack which have improved resin holding capacity while maintaining good water vapor permeability.

A further object of the present invention is to provide orthopedic casting materials having reduced tack which are significantly less expensive than other nonplaster of Paris prior art casting materials.

These and other objects and features of the present invention, as it relates to nonwoven fabrics, will become more fully apparent from the following description and appended claims, taken in conjunction with the accompanying drawings.

DESCRIPTION OF THE PREFERRED EMBODIMENTS WHICH UTILIZE NONWOVEN FABRICS

Figure 1A:
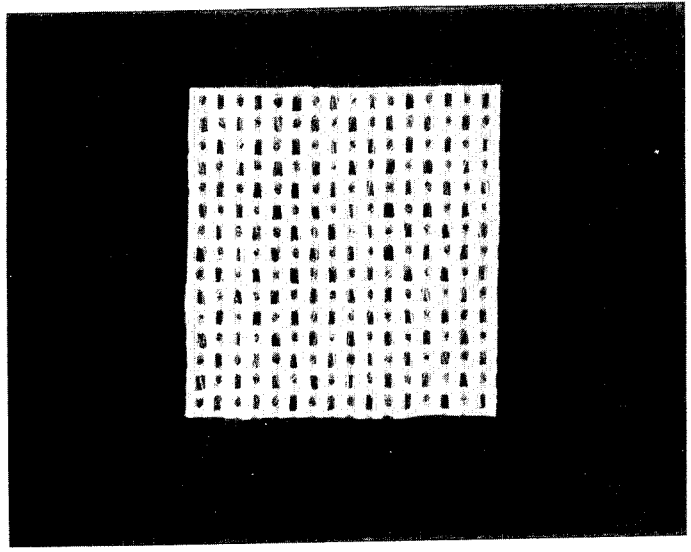
FIG. 1A is a photograph (taken to scale) of one presently preferred nonwoven fabric which can be used in accordance with the present invention, and which fabric is available from E.I. duPont de Nemours and Company, Textile Fibers Dept., Centre Road Bldg., Wilmington, Del., as Sontara ® polyester fabric, style 8043. In this and all other figures herein, the longitudinal or elongated direction of the nonwoven fabric is from top to bottom.
Figure 1B:
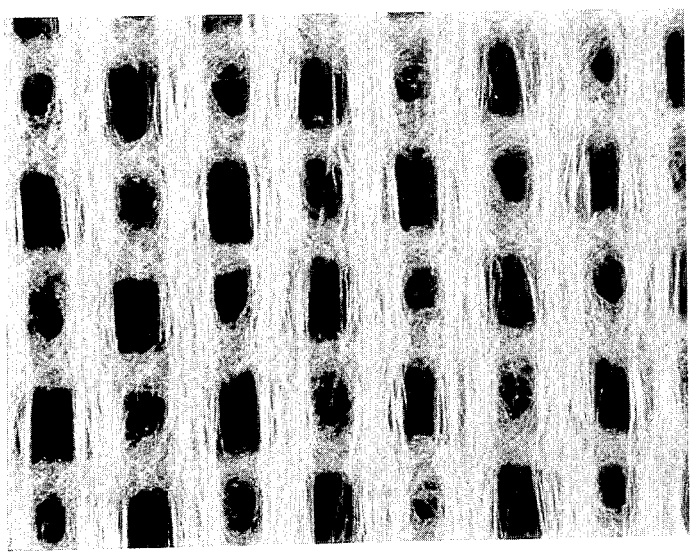
FIG. 1B is a photograph of a portion of the nonwoven fabric of FIG. 1A shown at a magnification of five times (5×) that of FIG. 1A.
Figure 1C:
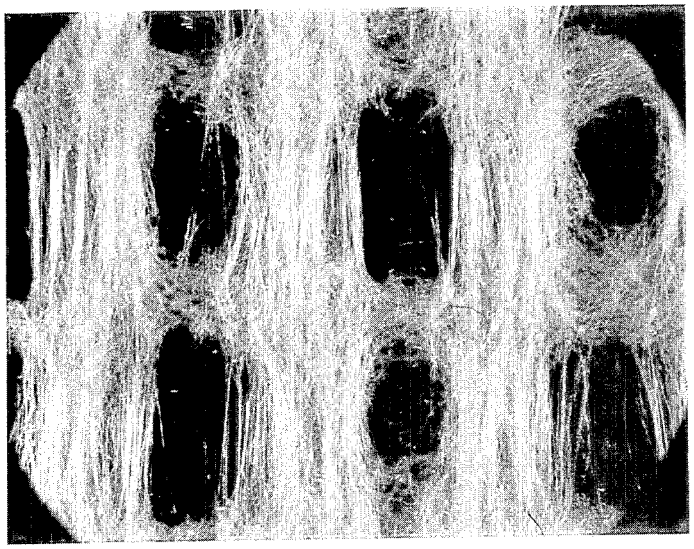
FIG. 1C is a photograph of a portion of the nonwoven fabric of FIG. 1A shown at a magnification of ten times (10×) that of FIG. 1A.
Figure 2A:
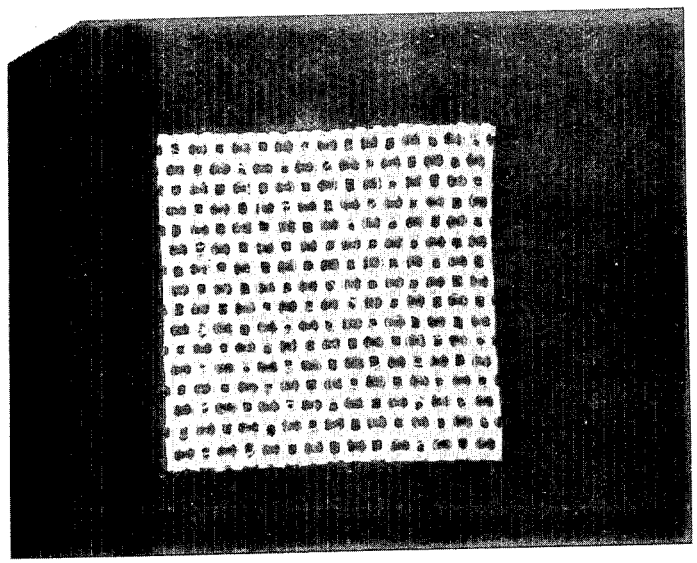
FIG. 2A is a photograph (taken to scale) of another presently preferred nonwoven fabric which can be used in accordance with the present invention, and which fabric is available from E.I. duPont de Nemours and Company as Sontara ® polyester fabric, conformable style 8043, set 2, 8 mesh, condition A.
Figure 2B:
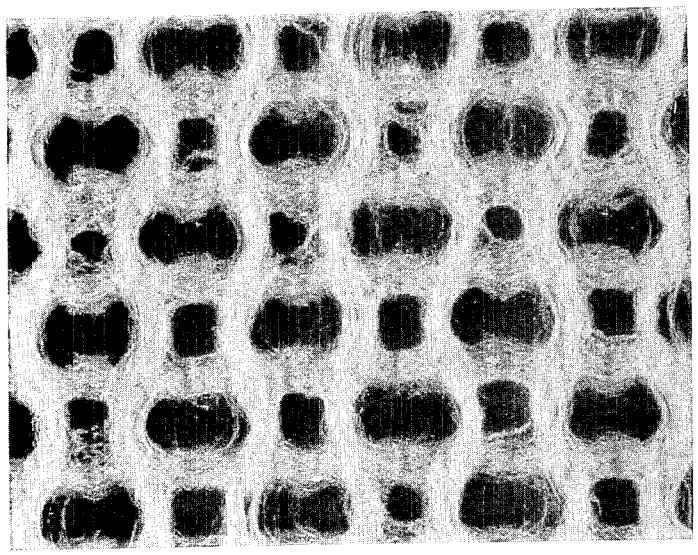
FIG. 2B is a photograph of a portion of the nonwoven fabric of FIG. 2A shown at a magnification of five times (5×) that of FIG. 2A.
Figure 2C:
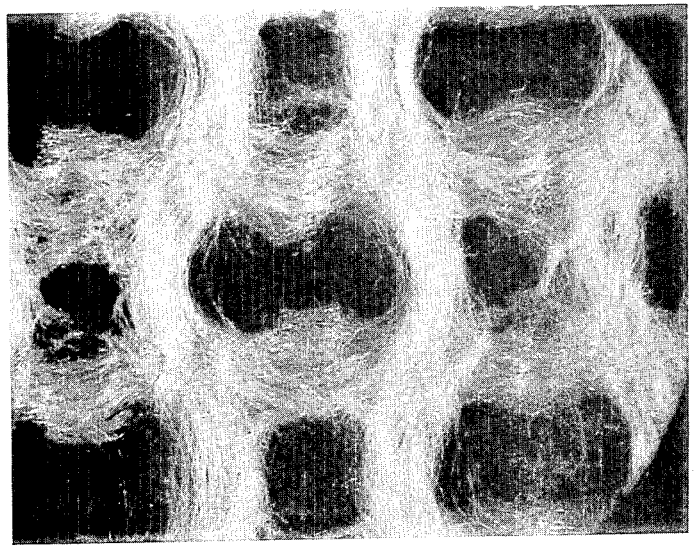
FIG. 2C is a photograph of a portion of the nonwoven fabric of FIG. 2A shown at a magnification of ten times (10×) that of FIG. 2A.

As stated, orthopedic casting materials may be prepared in accordance with the present invention, wherein the materials comprise a nonwoven, stretchable fabric which is impregnated with a curable prepolymer resin. In particular, the nonwoven fabrics employed in the present invention have important surface characteristics and physical properties which allow the nonwoven fabrics to be resin loaded to the extent needed to provide proper strength as an orthopedic casting material, while providing necessary porosity as well as improved tactile manipulability, moldability, and palpability. At the same time, the orthopedic casting materials of the present invention are relatively inexpensive, thus providing a more economical alternative to the non-plaster of Paris orthopedic casting materials presently known in the art which employ knitted fabrics.

In this regard, those skilled in the art have generally considered nonwoven fabrics undesirable as a support material or scrim in an orthopedic casting material which employs a curable resin, and have generally sought to use knitted materials alone for this purpose. However, applicants have discovered certain surface properties and other fabric characteristics which, when incorporated into a nonwoven fabric as disclosed herein, provide a fabric which can be resin loaded to the extent necessary to provide an orthopedic casting material having sufficient strength to be used efficaciously in forming an orthopedic cast or splint, while at the same time exhibiting the conformability and moisture vapor transmission necessary in orthopedic applications.

The stretchable, nonwoven fabric comprises fiber bundles and apertures between the fiber bundles, with each of the fiber bundles comprising a plurality of fibers having interstices therebetween. (Thus, the nonwoven fabrics of the present invention are sometimes referred to as "apertured," "ordered," or "patterned" nonwoven fabrics.) The fibers in each fiber bundle of the nonwoven fabric are preferably oriented so as to be generally parallel to one another. The interstices between the fibers of each fiber bundle receive the curable resin so as to impart strength to each fiber bundle upon curing. The generally parallel orientation of the fibers in each fiber bundle provides significantly greater resin holding capacity (and thus greater strength upon curing) than would be achieved if the fibers were randomly oriented. However, the apertures between fiber bundles, are substantially free of fibers such that, upon resin impregnation of the fiber bundles, the apertures remain substantially unoccluded so that sufficient water vapor permeability in the finished cast is preserved, and disadvantages such as potential skin maceration are substantially avoided.

The interstices between individual fibers and the apertures between fiber bundles for two presently preferred nonwoven fabric materials are seen in FIGS. 1A-1C and 2-2C. As seen in FIGS. 1A-1C and 2A-2C, the multiple fiber bundles of the nonwoven fabrics of the present invention form a matrix. Further, the characteristics of these fabrics after resin impregnation and lamination can be viewed in FIGS. 3A-3C and 4A-4C. The foregoing structural characteristics of the nonwoven fabrics of the present invention, in conjunction with the other characteristics and parameters disclosed herein, provide fabrics which can be resin loaded to the extent necessary to impart sufficient strength, while preserving air permeability through the material.

In conjunction with the structural configuration discussed above, the most important criteria for choosing a nonwoven fabric which will provide the characteristics necessary for purposes of the present invention include: (1) conformability, and the related characteristics of moldability, tactility, and palpabiltty once the fabric has been resin impregnated; (2) resin loading capacity; and (3) porosity. It is important that each of these parameters be carefully controlled in providing nonwoven fabrics which will successfully form orthopedic casting materials within the scope of the present invention.

Conformability is important from the standpoint that the nonwoven fabric must be extensible enough along its length, i.e., in the elongated direction, so that the resultant orthopedic casting material can be made to substantially conform to the body part to which it is applied. Materials which are not sufficiently extensible in the elongated direction do not conform well to the body part when wrapped therearound, often resulting in undesirable wrinkles or folds in the material. On the other hand, the extensibility of the nonwoven fabric in the elongated direction should not be so high that the material is too stretchy, resulting in a material structure which may be deformed to the extent that resin holding capacity and porosity are substantially reduced.

With these criteria in mind, for purposes of the present invention, the nonwoven fabric should have from about 10% to about 45% extensibility in the elongated direction when a 2 pound (908 gram) load or force is applied across a 1.5 inch (3.8 cm) section of the nonwoven fabric, and preferably from about 15% to about 30% extensibility in the elongated direction when a 2 pound (908 gram) load or force is applied across a 1.5 inch (3.8 cm) section of the nonwoven fabric.

Although not nearly as critical, it is also desirable that the nonwoven fabric employed have some extensibility along its width, i.e., in the direction transverse to the elongated direction. Thus, although the nonwoven fabric may have from 0% to 100% extensibility in the transverse direction, it is presently preferable to use a nonwoven fabric having from about 1% to about 30% extensibility in the transverse direction when a 2 pound (908 gram) load or force is applied across a 1.5 inch (3.8 cm) section of the nonwoven fabric.

The nonwoven fabrics of the present invention, although stretchable, are preferably not elastic or resilient. Thus, once the resin impregnated fabric has been stretched and applied around a body part, the stretched material maintains its shape and does not resort back to its unstretched position. The use of a nontacky resin as disclosed herein with the nonwoven fabric allows a roll of the resin-impregnated fabric to be unrolled quickly without undesirably stretching the material as it is unrolled. Hence, the material remains unstretched after being quickly unrolled, and is stretched only as it wrapped around the body part to be immobilized.

The resin loading capacity or ability of the nonwoven fabric to hold resin is important from the standpoint of providing n orthopedic casting material which has sufficient strength to efficaciously immobilize a body part. The surface structure of the nonwoven fabric, including the fibers and fiber bundles, interstices, and apertures discussed herein, is very important in providing proper resin loading for purposes of the present invention. In this regard, the interstices between the fibers of each fiber bundle must provide sufficient volume or space to hold an adequate amount of resin within the fiber bundle to provide the strength necessary; while at the same time, the apertures between fiber bundles must remain sufficiently unoccluded such that adequate porosity is preserved once the resin is applied. (Generally parallel orientation of the fibers in the fiber bundles provides interstices which optimize resin holding capacity and resultant strength of the material upon curing.) Thus, the interstices between fibers are important in providing the necessary resin loading capacity, while the apertures are important in providing the necessary porosity for the finished cast. However, a balancing of various parameters is needed to achieve both proper resin loading and porosity.

For purposes of the present invention, it has been found that the nonwoven fabric should be structured such that is can be resin loaded to the point where the resin represents from about 65% to about 90% by weight of the total weight of the orthopedic casting material, and preferably from about 80% to about 87% by weight of the orthopedic casting material. Further in this regard, it has been found that in order to provide proper resin loading within the scope of the present invention, from about 0.1 to about 0.3 grams of resin should be applied to each square inch of the nonwoven fabric, with the preferred range of resin loading being from about 0.16 to about 0.24 grams of resin per square inch of nonwoven fabric. If resin loading significantly less than that disclosed herein is employed, the lamination strength of the orthopedic casting material will be compromised. On the other hand, if resin loading significantly higher than that disclosed herein is employed, porosity may be sacrificed by the undesirable occlusion of the apertures of the nonwoven fabric.

Other factors which are helpful in providing for proper resin loading of the nonwoven fabric of the present invention include the average cross-sectional area covered by each fiber bundle, the average number and size of fibers in each fiber bundle, the average volume or space between fibers in each fiber bundle, and the basis weight of the nonwoven fabric employed. In this regard, it has been found desirable to select a nonwoven fabric wherein the transverse cross-section of each fiber bundle of the nonwoven fabric covers an average area of from about 0.2 mm$^2$ to about 1.2 mm$^2$, and preferably from about 0.4 mm$^2$ to about 1 mm$^2$. Further, it is desirable that each fiber bundle contain an average of at least about 100 fibers along a given cross-section, and preferably at least about 200 fibers. The average diameter of the individual fibers in each fiber bundle is preferably from about 1 micron to about 30 microns, and most preferably from about 5 microns to about 20 microns. Additionally, of the total volume occupied by a given fiber bundle (including both fibers and interstices), it is desirable that the average volume defined by the interstices alone (also known as the void volume) represent from about 20% to about 98% of such total volume, and preferably from about 70% to about 96% of the total volume. Moreover, it is desirable to use a nonwoven fabric having a basis weight of from about 1 ounce per square yard (34.0 g/m$^2$) to about 2.5 ounces per square yard (84.9 g/m$^2$), and preferably from about 1.2 ounces per square yard (40.8 g/m$^2$) to about 2.1 ounces per square yard (71.3 g/m$^2$).

The range of values given above for the average volume defined by the interstices (or average void volume) for the various nonwoven fabrics within the scope of the present invention was determined using the following procedure. First, a representative fiber bundle was taken from each nonwoven fabric and mounted in epoxy. Next, thin cross-sections of each fiber bundle were microtomed from this. The number of fibers per bundle was estimated under magnification (53×) with cross polarized light. The cross-sectional area of the fiber bundle was estimated from a photomicrograph (taken at 53× magnification) The average fiber diameter was estimated by examining the individual fibers at 400× magnification. The total estimated volume occupied by the fiber bundle and the estimated volume occupied only by the fibers in the bundle were then calculated. The estimated volume occupied by the fibers was then subtracted from the total estimated volume of the fiber bundle, and this difference was divided by the total estimated volume of the fiber bundle and multiplied by 100 to give the estimated percent void volume.

As mentioned, porosity is also an important characteristic for the nonwoven fabrics of the present invention. If the orthopedic casting material is not sufficiently porous after curing, skin maceration and other undesirable problems may occur. As will be appreciated from the discussion herein relating to resin loading of the nonwoven fabric, porosity and resin loading are often influenced by similar factors, and thus a balance must be achieved. (For example, where a nonwoven fabric is employed having a basis weight towards the lower end of the ranges set forth herein, resin loadings at the lower end of the ranges set forth herein may be most suitably employed. Conversely, when higher basis weights are employed, higher resin loadings are generally more suitable.)

Of key importance in providing adequate porosity is the number of apertures per unit area and the size of the apertures between the fiber bundles. In this regard, it has been found desirable to use a nonwoven fabric having, in its unstretched state, from about 15 to about 400 apertures per square inch of nonwoven fabric, and preferably, from about 35 to about 170 apertures per square inch of nonwoven fabric. Additionally, it is desirable to use a nonwoven fabric having an average aperture size of from about 0.3 size of from square millimeters (0.3 mm$^2$) to about 16 mm$^2$, and preferably having an average aperture about 1.2 mm$^2$ to about 9 mm$^2$. Aperture sizes significantly lower than those disclosed herein typically do not allow sufficient air permeability to provide the porosity needed for a suitable orthopedic casting material. Aperture sizes much greater than those disclosed herein result in an aesthetically undesirable increase in surface roughness, and may not provide enough fiber bundles per unit area such that resin loading of the fiber bundles can result in a material having sufficient strength in relatively few layers.

The aperture sizes disclosed herein are large enough that the resin will migrate to and associate with the fiber bundles so as to leave the apertures substantially unoccluded. In this regard, it is desirable that an average aperture size be selected such that, when resin loading within the ranges disclosed herein is employed, from about 60 to about 100% of the total area of the apertures remains unoccluded after impregnation of the nonwoven fabric with the curable resin, and preferably such that from about 75% to about 100% of the total area of the apertures remains unoccluded after resin impregnation. By so doing, sufficient air permeability can be achieved so that adequate water vapor transmission in the finished cast is provided.

For purposes of the present invention, the total area of the apertures remaining unoccluded after resin impregnation of each nonwoven fabric was determined as follows. First, a 3 inch (7.6 cm) by 8 inch (20.3 cm) piece of each fabric was cut out, and two areas about 1.5 cm by 1.5 cm were selected and marked. A photograph of each marked area was then taken at 5× magnification. The piece of fabric was then impregnated with the desired amount of curable resin by spreading the resin onto the fabric and manually kneading the resin into the fabric until evenly distributed, and photographs of the two marked areas were again taken at 5× magnification. In each photograph of uncoated fabric, twenty apertures were selected and measured, and the same apertures were located and measured in the photographs taken after resin impregnation. The selected apertures were measured in each photograph by estimating the length and width in millimeters at approximately the middle of each aperture. The mean area of the apertures in each marked area of the fabric before and after resin impregnation was then estimated by first dividing the length and width measured in the photographs by 5 (to compensate for the magnification factor), and then multiplying the resultant two figures together. By subtracting the mean aperture area of the resin impregnated fabric from that of the uncoated fabric, and dividing the result by the mean aperture area of the uncoated fabric, the fraction of aperture area occluded by resin was calculated. The percentage of the total aperture area remaining unoccluded by resin was then determined by subtracting the above number from 1 and then multiplying by 100.

By employing nonwoven fabrics having the characteristics discussed herein, orthopedic casting materials are provided which have good water vapor permeability for orthopedic applications. Upon curing a 6 layer ring laminate of the orthopedic casting material, the laminate has a passive water vapor permeability of at least about 2000 milligrams of water vapor per square meter of material per hour (2000 mg $H_2O$ vapor/$m^2$-hr) when measured under an atmosphere of about 45% relative humidity and at a temperature of about 72° F. (22° C.), and in the most preferable embodiments of the present invention, at least about 2200 mg $H_2O$ vapor/$m^2$-hr when measured under the same conditions.

The passive water vapor permeability of orthopedic casting materials made in accordance with the present invention has been measured using the following procedure. Test rings having an inside diameter of 2 inches (5.1 cm) and a length of 3 inches (7.6 cm) were first prepared from the orthopedic casting materials by dipping the materials in water for about 30 seconds at room temperature and wrapping 6 layers of each material around a polyester stockinet covered aluminum mandrel having a 2 inch (5.1 cm) diameter. The layers were smoothed down with light hand pressure, and after becoming rigid, each ring was removed from the mandrel (with the stockinet adhering to the inside of the ring) and allowed to dry and cure at room temperature for at least 24 hours. After such time, one end of each ring was sealed with a plastic petri dish using a silicone based sealant, namely RTV 732 Silastic ™, available from Dow Corning, Midland, Mich. A small beaker containing about 30 grams of water was placed inside each ring, and the other end of each ring was then also sealed with a plastic petri dish using RTV 732 Silastic ™. Each sample so prepared was initially weighed, and then weighed at periodic intervals until over 300 hours had elapsed. The amount of water vapor having passed through each ring was then determined by calculating the difference in weight from start to finish.

When an air pressure differential of about 6.4 psi (absolute) or 449 g/$cm^2$ is imposed between two sides of a 6 layered laminate (with each layer having an area of about 4 $in^2$) of the cured orthopedic materials of the present an air permeability of from about 30 $cm^3$ air/second to about 370 $cm^3$ air/second is achieved, with an air permeability of from about 90 $cm^3$ air/second to about 370 $cm^3$ air/second being observed in the most presently preferred embodiments of the present invention. (Although the relative humidity and temperature are not as critical here as for the passive water vapor permeability tests, it should be noted that these forced air permeability values were determined under an atmosphere of about 45% relative humidity and at a temperature of about 22° C., in accordance with the procedure outlined below). Thus, it is evident that the present invention provides the air permeability necessary and important to orthopedic applications.

For purposes of the present invention, the air permeability of each cured material was determined as follows. First, 2 inch (5.1 cm) by 48 inch (121.9 cm) strips of each fabric were cut out, impregnated with the desired amount of curable resin, fan folded, and sealed in an air-tight pouch. Later, each pouch was opened, the folded strip of fabric was dipped in room temperature tap water for about 30 seconds, and then a six layer laminate (each layer being about 2 inches (5.1 cm) by 2 inches (5.1 cm)) was made by quickly unfolding the wet strip and fan folding it onto a polyester stockinet lying on a flat surface until six layers were formed; the strip was cut and the procedure repeated four times to form four different laminates. The six layers in each laminate were secured together by firmly rubbing an extended finger across each laminate and then continuing to smooth each laminate with light finger pressure until set. After setting, each laminate was separated from its respective stockinet. Twelve hours later, a ½ inch (1.3 cm) diameter disk of Microfoam ® brand tape (3M) was placed on each side of each laminate in approximately the center so that the disks were lined up, one directly above the other. Each laminate was then coated over both surfaces with RTV 732 sealant (Dow Corning, Midland, Mich.) to occlude the unmasked areas and provide a gasket for the air permeability measuring device. The sealant was cured by placing each coated laminate in an oven at 120° F. (49° C.) for at least 2 hours. Each coated laminate was then in turn placed between the upper and lower clamping plates of a Gurley Densometer No. 4110, and the lower plate was raised to seal the laminate between the plates with the masked area approximately centered. The inner cylinder was freed to sink. If the cylinder stopped sinking or sank only very slowly, the seal was considered adequate. (Otherwise, another layer of RTV sealant was applied to both sides and cured.) The laminate was then removed from the Densometer, and the Microfoam tape was removed exposing a ½ inch (1.3 cm) diameter circular area of substrate on both sides of the laminate. The laminate was then again clamped between the plates and the time measured for the inner cylinder (weighing 20 oz.) to drop a distance corresponding to the passage of 300 $cm^3$ of air under a pressure differential of 6.4 psi (absolute) or 449 g/$cm^2$. This was repeated three more times, and the longest time noted for each laminate was taken as a measure of its air permeability. The volume of air passed per second was calculated by dividing 300 $cm^3$ by the mean time determined on 4 samples for passage of this volume of air.

Although apertured and stretchable nonwoven fabrics meeting the criteria set forth herein may be prepared by various methods, the presently most preferred nonwoven fabrics are prepared by well-known techniques which yield what are known as "spunlaced" and "hydroentangled" nonwoven fabrics. The term "spunlaced fabric" generally refers to a nonwoven fabric formed of fibers entangled in a predetermined and repetitive pattern to form a strong structure free of binder material. Typically, in producing a spunlaced fabric, a fibrous support web is subjected to high velocity water jets that entangle the fibers and thereby achieve mechanical bonding of the fibers. This process is the reason that such nonwoven fabrics are typically referred to as "hydroentangled fabrics," the fabrics being formed through entanglement achieved by water jets. In this regard, the high pressure water jets typically entangle the fibers at velocities of up to 100 meters/second. The fibrous support web is patterned in accordance with the desired pattern of the nonwoven fabric to be formed. Thus, when the jets of water are applied both above and beneath the fibrous support web, the fibers are oriented into a pattern of fiber bundles and apertures according to the pattern on the fibrous support web.

Processes such as that disclosed herein for forming spunlaced and hydroentangled nonwoven fabrics are well known to those skilled in the art. One such process is detailed, for example, in *Guide to Nonwoven Fabrics*, (1978), published by the INDA Association of the Nonwoven Fabrics Industry, 1700 Broadway (25th Floor), New York, N.Y. 10019, which publication is incorporated herein by reference. Additionally, spunlaced and hydroentangled nonwoven fabrics and processes for preparing the same are disclosed in U.S. Pat. No. 3,485,706, which is also incorporated herein by reference.

The selection of an appropriate material for the nonwoven fabrics of the present invention is necessarily influenced by the fact that the resultant nonwoven fabric must have the properties outlined herein. Preferably, for purposes of the present invention, the material is also relatively inexpensive. Relatively inexpensive materials which have been found suitable for the nonwoven fabrics of the present invention include polyester materials which may be easily processed at relatively low cost or which may be readily obtained. Such polyester nonwoven fabrics are presently preferred.

The presently most preferred nonwoven fabric materials are the Sontara® polyester fabrics, which are spunlaced and hydroentangled fabrics manufactured by E.I. duPont de Nemours and Company, Textile Fibers Dept., Centre Road Bldg., Wilmington, Del. More particularly, the nonwoven polyester fabrics known as Sontara® polyester fabric, style 8043 and Sontara® polyester fabric, conformable style 8043, set 2, 8 mesh, condition A are materials which have been found to work extremely well for purposes of the present invention. These two polyester fabrics are the subject of FIGS. 1A–1C and 2A–2C, respectively.

The nonwoven polyester fabric materials such as the Sontara® polyester materials referenced herein exhibit all of the desirable and necessary properties outlined herein for successfully practicing the present invention. Further, these nonwoven polyester fabric materials have been found to have high bulk at low weight, good conformability, good wet and dry strength per unit of weight, good cover and uniformity, do not unravel or delaminate, and are inherently low linting.

Other materials which may be used to form the nonwoven fabrics of the present invention include cotton, nylon, acrylic, polypropylene, fiberglass, polyarlamide, and carbon (graphite). These materials, however, are not presently preferred over the above-mentioned polyester materials, primarily because of their increased cost. In this regard, cotton, nylon, acrylic, polypropylene, and fiberglass are somewhat more expensive than the preferred polyester materials, while polyarylamide and carbon are quite significantly more expensive.

Moreover, those skilled in the art will recognize that fiberglass nonwoven materials have a significantly higher density than the other materials disclosed herein. Thus, when fiberglass nonwoven materials are employed, the basis weight of the material and weight percent of resin employed will vary from the values set forth herein. In this regard, when fiberglass is used, the nonwoven fabric should have a basis weight of from about 1.8 ounces per square yard (61.1 $g/m^2$) to about 4.6 ounces per square yard (156.3 $g/m^2$), preferably from about 2.2 ounces per square yard (74.7 $g/m^2$) to about 3.6 ounces per square yard (122.3 $g/m^2$), and the fiberglass nonwoven fabric should be resin loaded such that the resin represents from about 35% to about 90% by weight of the total weight of the orthopedic casting material, preferably from about 50% to about 87% by weight.

The importance of selecting a nonwoven fabric in accordance with the criteria set forth herein is further seen in view of the number of nonwoven fabrics which are not suitable for purposes of the present invention, including for example, bonded air-laid or carded web materials, wet formed random bonded web materials, Thinsulate® brand blown microfiber web materials, and thin foam materials.

In this regard, although bonded air-laid or carded web materials coated with resin have fair porosity and good strength upon curing, the resin holding capacity of such materials is not sufficient nor is the degree of extensibility needed for proper conformability sufficient for purposes of the present invention. Similarly, wet formed random bonded web materials suffer from poor resin holding capacity and poor conformability, and when coated with a resin, such materials also exhibit poor porosity. Further, although the Thinsulate® brand blown microfiber web materials exhibit relatively good resin holding capacity, the cohesion of the scrim structure and porosity of the cured products formed from these materials are inadequate for purposes of the present invention. Additionally, although thin foam materials (having a thickness of 1/16 of an inch or less) have good conformability, these materials also exhibit inadequate resin holding capacity to be used with the present invention. The failure of these and other nonwoven fabrics or materials demonstrates the need to balance resin holding with porosity, conformability with tensile strength (cohesion), and ultimate structural strength with material tactility (the ability to feel through the fabric). Hence, the selection of an appropriate nonwoven fabric in accordance with the criteria set forth herein is very important to the successful practice of the present invention.

The curable resins impregnated into the nonwoven fabrics of the present invention are generally flowable at room temperature. Although such flowability could well result in the escape or loss of significant amounts of resin from other more conventional nonwoven materials, the exceptional resin holding capacity of the nonwoven fabrics of the present invention substantially prevents such escape or loss.

The curable resins which may be used to impregnate the nonwoven fabrics of the present invention include any resins which will provide the resin loading and porosity characteristics outlined herein. Preferred resins include isocyanate functional, polyurethane prepolymer resins. When using such resins, orthopedic casting materials can be prepare which, upon reaching full cure, exhibit a ring strength of at least about 10 pounds/inch (pounds per inch of cylinder length when using a cylinder 3 inches (7.6 cm) long and 2 inches (5.1 cm) in diameter which is prepared in accordance with the procedure set forth herein for preparing 6 layer test rings useful in the determination of passive water vapor permeability) or 1.79 kg/cm, with ring strengths of at least about 20 pounds/inch or 3.57 kg/cm being characteristic of the most presently preferred embodiments of the present invention. That such strength can be achieved by resin loading a nonwoven fabric in accordance with the present invention is one of the surprising benefits which has been discovered. Other surprising benefits include the relative smoothness of the resultant orthopedic casting material and the ability of the material to resist fraying.

The curable resins used with the nonwoven fabrics of the present invention are crosslinkable to a thermoset state. Preferably, the curable resins have viscosities within the range of from about 5000 centipoise to about 500,000 centipoise, and most preferably within the range of from about 10,000 centipoise to about 100,000 centipoise. The resin should be nontoxic in the sense that it does not give off significant amounts of toxic vapors during curing which may be harmful to either the patient or the person applying the orthopedic casting material, and also in the sense that it does not cause skin irritation either by chemical irritation or by the generation of excessive heat during cure. Furthermore, the resin must be sufficiently reactive with the curing agent, (e.g., water, where water curable resins are concerned) to ensure rapid hardening of the orthopedic casting material once it has been applied, but not so reactive that it does not allow for sufficient working time to apply and shape the orthopedic cast or splint. Initially, the orthopedic casting material must be pliable and conformable and should adhere to itself. Then in a short time following the completion of application, it should become rigid, or at least semirigid, and strong enough to support the loads and stresses to which the cast or splint is subjected by the activities of the wearer. Thus, the orthopedic casting material must undergo a change of state from a flexible condition to a relatively rigid condition in a matter of minutes.

The presently preferred resins for use with the nonwoven fabrics are those which are cured with water. A number of classes of water curable resins are known in the art and are suitable for purposes of the present invention, including polyurethanes, cyanoacrylate esters (preferably used in conjunction with a suitable filler material such as polycyanoacrylate), and, when combined with moisture sensitive catalysts, epoxy resins and prepolymers terminated at their ends with trialkoxysilane or trihalo-silane groups. With regard to the epoxy resins, it is noted that U.S. Pat. No. 3,932,526 discloses 1,1-bis(perfluoromethylsulfonyl)-2-aryl ethylenes which cause epoxy resins containing traces of moisture to become polymerized.

Resin systems other than those which are water curable may be used with the nonwoven fabrics of the present invention, although the use of water to activate the hardening of the orthopedic casting materials is presently the most convenient, safe, and familiar to orthopedic surgeons and medical casting personnel. For example, resin systems employing difunctional acrylates or methacrylates, such as the bis-methacrylate ester disclosed in U.S. Pat. No. 3,908,644, which ester is derived from the condensation of glycidyl methacrylate and bisphenol A (4,4'-isopropylidenediphenol), may be used. Such a resin system is hardened upon wetting with solutions of a tertiary amine and an organic peroxide. Further, U.S. Pat. No. 3,630,194 discloses an orthopedic tape impregnated with acrylamide monomers whose polymerization is initiated by dipping the orthopedic tape in an aqueous solution of oxidizing and reducing agents (known in the art as a redox initiator system).

The presently preferred resins used in conjunction with the nonwoven fabrics of the present invention cure to form a relatively rigid structure or cast. However, in some instances such as sports medicine applications, a somewhat flexible resin may be desired to form a semirigid and resilient support upon curing. Examples of suitable flexible resins which may be used for this purpose are disclosed in commonly assigned copending patent application Ser. No. 903,281, filed Sept. 3, 1986, which is incorporated herein by reference.

As mentioned, the presently most preferable resins used with the nonwoven fabrics of the present invention are water curable, isocyanate functional, polyurethane prepolymer resins. These resins are prepared by reacting a polyisocyanate with a polyol, as disclosed, for example, in U.S. Pat. Nos. 4,411,262 and 4,502,479. However, other urethane resins formed by the reaction of a polyisocyanate and a polyol, such as disclosed in U.S. Pat. No. 4,131,114, may also be used.

Thus, as used herein, a "water curable, isocyanate functional, polyurethane prepolymer" means a prepolymer derived from a polyisocyanate, preferably aromatic, and a polyol (or reactive hydrogen compound or oligomer). The polyurethane prepolymer has sufficient isocyanate functionality to cure upon exposure to water, either in the form of moisture vapor, or more preferably, in the form of liquid water.

In forming the preferred water curable, isocyanate functional, polyurethane prepolymers for use with the nonwoven fabrics of the present invention, it is preferred to use an isocyanate which has a relatively low volatility, such as diphenylmethane diisocyanate (MDI), rather than a more volatile material such as toluene diisocyanate (TDI). Presently preferred isocyanates include 4,4'-diphenylmethane diisocyanate, 2,4'-diphenylmethane diisocyanate, and mixtures of these isomers together with possible small quantities of 2,2'-diphenylmethane diisocyanate (typical of commercially available diphenylmethane diisocyanate). However, isocyanates such as aromatic polyisocyanates and their mixtures which are derived from phosgenation of the condensation product of aniline and formaldehyde may also be used.

Polyols which may be used to form the polyurethane prepolymers for use with the nonwoven fabrics of the present invention include polypropylene ether glycols (available from Union Carbide, Danbury, Conn. as Niax TM PPG and from BASF Wyandotte Corp., Parsippany, N.J. as Pluracol TM P), polytetramethylene ether glycols (available from the Quaker Chemical Company, Conshohocken, Pa. as Polymeg TM), polycaprolactone diols (available from Union Carbide as the Niax TM PCP series of polyols), and polyester polyols (hydroxyl terminated polyesters obtained from the esterification of dicarboxylic acids and diols such as the Lexorez TM polyols available from Inolex Corp., Chemical Division, Philadephia, Pa.). As will be appreciated by those skilled in the art, the rigidity of the cured resin can be reduced by increasing the molecular weight of the polyols, or conversely, the rigidity can be increased by using lower molecular weight polyols.

It will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957). Thus, for example, thiols and polyamines could also be used as "polyols" in the present invention, and the term "polyols" will be considered to include such other active hydrogen compounds.

One example of a presently preferred resin which may be used with the nonwoven fabrics of the present invention involves the reaction of an isocyanate known as Isonate TM 143L (a mixture containing about 73% MDI) which is available from the Upjohn Company, LaPorte, Tex. with a polypropylene oxide polyol which is available from Union Carbide and is known as Niax TM PPG 725. To prolong the shelf life of the resin material, it is also preferable to include from about 0.01% to about 1% by weight of benzoyl chloride or other suitable stabilizer.

The reactivity of the curable resin, once it is exposed to the water or other curing agent, can be controlled by the use of a proper catalyst. The reactivity must not be so great that: (1) a hard film quickly forms on the resin surface preventing further penetration of the water into the bulk of the resin, or (2) the cast or splint becomes rigid before the application and shaping thereof has been completed. To produce suitable orthopedic casts and splints in accordance with the present invention, a set time of from about 2 to about 18 minutes following activation of the curable resin is preferred, with the most preferable set time being from about 3 to about 10 minutes. Thus, the curable resins of the present invention also preferably contain a catalyst to control the set time and cure time of the resin.

Suitable catalysts for moisture curing polyurethane prepolymer resin systems are well known. For example, tertiary amine catalysts such as 2,2'-dimorpholinodiethylether (DMDEE) described in U.S. Pat. No. 4,433,580, bis(2,6-dimethylmorpholino)diethylether described in U.S. Pat. No. 4,574,793, and 4-[2-[1-methyl-2-(4-morpholinyl)-ethoxy]ethyl]-morpholine (MEMPE) described in commonly assigned, copending patent application Ser. No. 784,344, filed Oct. 4, 1985, in amounts ranging from about 0.5% to about 5% by weight of the resin system, may be used for this purpose. The MEMPE catalyst disclosed in patent application Ser. No. 784,344, filed Oct. 4, 1985, which application is incorporated herein by reference, is the presently preferred catalyst system for use in connection with the present invention.

Foaming of the resin which would reduce the porosity of the cured material and its overall strength should be minimized. Foaming occurs because carbon dioxide is released when water reacts with isocyanate groups. The most satisfactory method of minimizing foaming involves the addition of a foam suppressor such as silicone Antifoam A (Dow Corning, Midland, Mich.), DB-100 silicone fluid (Dow Corning), or silicone surfactant L550 or L5303 (available from Union Carbide) to the resin. It is presently preferred to use the Dow Corning DB-100 silicone fluid at a concentration of about 0.1% to about 1% by weight of the resin.

The preparation of orthopedic casting materials employing the nonwoven fabrics of the present invention generally involves the simple coating of the curable resin onto the nonwoven fabric. The wicking action of the fiber bundles assists in pulling the resin into the interstices, and manual manipulation of the resin into the nonwoven fabric is usually not necessary. It is important, however, that such coating result in sufficient impregnation of the curable resin into the interstices between the fibers of the fiber bundles of the nonwoven fabric. Thus, some manipulation or kneading of the resin into the fabric may sometimes be desirable. Care should be given not to stretch the nonwoven fabric during resin coating so as to preserve the stretchability of the material for its later application around the desired body part.

Orthopedic casting materials prepared in accordance with the present invention are applied in the same fashion as other known orthopedic casting materials. First, the animal body member or part to be immobilized is preferably covered with a conventional cast pad or stockinet to protect the body part. Next, the curable resin is activated, for example, by dipping the orthopedic casting material in water in the case of a water curable resin. Excess water is then squeezed out of the orthopedic casting material, and the material is wrapped or otherwise positioned around the animal body part so as to properly conform thereto. Preferably, the material is then molded and smoothed to form the best fit possible and to properly secure the bone and limb in the desired position. Although often not necessary, if desired, the orthopedic casting material may be held in place during cure by wrapping a stretch bandage or other securing means around the curing orthopedic casting material. When curing is complete, the animal body part is properly immobilized within the orthopedic cast or splint which is formed.

Because of the unique properties of the orthopedic casting materials employing the nonwoven fabrics of the present invention, good tactility and palpability are experienced. Thus, during application of the material to the injured body part, the applier can easily feel through the material to the bone structure therebeneath.

The present invention will be further understood in view of the following examples, which examples are merely illustrative and are not to be considered as comprehensive or limiting in any way.

EXAMPLE 31

In this example, orthopedic casting materials within the scope of the present invention were prepared as follows. First, a spunlaced, hydroentangled scrim of nonwoven polyester, having a basis weight of about 2.1 ounces per square yard (71.3 g/m$^2$), was obtained from E.I. duPont de Nemours and Company as Sontara ® polyester fabric, style 8043. (This is the nonwoven fabric shown in FIGS. 1A-1C.) This nonwoven polyester fabric had about 64 openings per square inch, with an average aperture size of about 1.3 mm×2.0 mm. This material was also observed to have an average fiber bundle cross-sectional area of about 65 mm$^2$, an average of about 417 fibers per fiber bundle along a given cross-section, an average fiber diameter of about 12 microns, and an average estimated void volume within each fiber bundle of about 93%. Further, the nonwoven polyester fabric had an extensibility of about 22% (when a 2 lb.

(908 gram) load was applied across a 1.5 inch (3.8 cm) section of the fabric) in the elongated direction and an extensibility of about 3% (when a 2 lb. (908 gram) load was applied across a 1.5 inch (3.8 cm) section of the fabric) in the transverse direction.

In this Example 31 and all other examples where nonwoven fabrics were employed, the extensibility of the nonwoven fabric was measured by placing a 4 inch×4 inch (10.2 cm×10.2 cm) piece of the nonwoven fabric in the grips (each grip measuring 1.5 inches (3.8 cm) wide) of a model 1122 Instron Tensile tester so as to engage a 1.5 inch (3.8 cm) section of the nonwoven fabric. The grips were spaced 1 inch (2.5 cm) apart. The tester was equipped with a 50 lb. (22.7 kg) load cell, which was set for a crosshead speed of 2 inches (5.1 cm) per minute, and a chart speed of 2 inches (5.1 cm) per minute, and an increasing load was applied until a load of 2 pounds (908 grams) was imposed across the 1.5 inch (3.8 cm) section of the fabric. The total distance that the nonwoven fabric was stretched immediately upon reaching the 2 pound (908 gram) load, divided by the original length of the fabric between the grips (namely, 1 inch (2.5 cm)), was multiplied by 100 to give the percent extensibility or elongation. A load of 2 pounds (908 grams) was chosen in an attempt to approximate the maximum tension which is typically needed when applying an orthopedic casting material to a broken or injured limb.

In this Example 31, several strips of the nonwoven polyester fabric were employed having various dimensions. In this regard, strips were cut having the following dimensions: 1) about 3 inches (7.6 cm) wide and about 144 inches (365.8 cm) long; 2) about 3 inches (7.6 cm) wide and about 41 inches (104.1 cm) long; and 3) about 2 inches (5.1 cm) wide and about 48 inches (121.9 cm) long. These strips were cut such that the length of the strips was coincident with the elongated direction of the fabric material. These strips of fabric were then coated with an isocyanate functional, polyurethane prepolymer resin, such that about 0.20 grams of the resin were applied to each square per inch of the nonwoven fabric (0.031 grams/cm$^2$). Such a resin loading resulted in an orthopedic casting material wherein the resin represented about 82% by weight of the total weight of the material.

The polyurethane prepolymer resin which was utilized in this Example 31 was prepared by the following procedure. A stainless steel reactor was used and was equipped with an axial flow impeller, a nitrogen purge line holding the reactor at a small positive nitrogen pressure, an inlet line for pumping reactants into the reactor, an addition port for adding smaller amounts of chemicals, heating and cooling means, and a stainless steel funnel. The following chemicals listed according to their relative amounts were combined in the reactor as described below.

| Chemical | Wt (%) |
|---|---|
| Isonate 143L (Upjohn) | 58.25 |
| Benzoyl chloride | 0.05 |
| Pluronic F-108 (BASF) | 3.95 |
| DB-100 silicone fluid (Dow Corning) | 0.18 |
| 2,6-Di-tert-butyl-4-methyl phenol (BHT) | 0.48 |
| Niax PPG 425 (Union Carbide) | 6.74 |
| Niax PPG 725 (Union Carbide) | 29.03 |
| MEMPE catalyst | 1.32 |

The Isonate 143L was first pumped into the reactor and agitated by starting the impeller. The MEMPE catalyst was then pumped in, and after about 5 minutes of mixing, the Pluronic F-108 was poured into the reactor using the stainless steel funnel. After about 10 minutes of further mixing, the DB-100 silicone fluid was added through the small chemical addition port followed by the addition of the benzoyl chloride in the same manner. After about 5 minutes of further mixing, the Niax PPG 425 polyol was pumped in followed by the BHT which was dissolved in about 15% of the total Niax PPG 725 polyol, and then the remaining 85% Niax PPG 725 polyol was added. The mixture was then held at a temperature of about 150° F. (65° C.) with constant agitation for approximately 2 hours and then cooled to room temperature. Within a moisture free chamber, the resultant resin was spread onto the fabric strips, and evenly distributed by manually kneading the resin into the fabric strips.

Following resin impregnation, it was observed that the apertures of the resin impregnated strips were substantially unoccluded. In this regard, the resin adhered to the fiber bundles and kept clear of the apertures such that the averages unoccluded area of the apertures after resin impregnation was measured to be about 1.1 mm×1.8 mm, or about 77% of the total area of the apertures. Each resin impregnated strip was then individually sealed in an airtight and water impermeable pouch for later use.

Later, one of the resin impregnated strips (measuring 3 inches (7.6 cm) by 144 inches (365.8 cm)) was removed from its pouch, dipped in water to activate the resin, and excess water was squeezed out. A forearm cast was then constructed by wrapping the resin impregnated strip around a human arm to which a protective stockinet and cast padding had been previously applied. Water penetration to the core of the material was observed. The material came off of the roll quickly and without stretching, and the material was relatively easy to apply. In this regard, the resin impregnated material demonstrated excellent conformability and extensibility, and allowed for the palpation of the bone structure through the applied material. The cured cast was very smooth and conformed well to the contours of the forearm with little, if any, wrinkling.

When tested, cured ring laminates (having 6 layers) formed from the resin impregnated strips (measuring 3 inches (7.6 cm) by 41 inches (104.1 cm)) of this Example 31 were found to have an average passive water vapor permeability of about 2200 mg H$_2$O vapor/m$^2$-hr (when measured under an atmosphere of about 45% relative humidity and at a temperature of about 22° C.). Four cured flat laminates (having 6 layers, each measuring 2 inches (5.1 cm) by 2 inches (5.1 cm)) formed from one of the resin impregnated strips (measuring 2 inches (5.1 cm) by 48 inches (121.9 cm)) of this Example 31 were found to have an average air permeability of about 94 cm$^3$ air/second when an air pressure differential of about 6.4 psi (absolute) or 449 g/cm$^2$ was imposed between the two sides of the laminate.

Figure 3A:
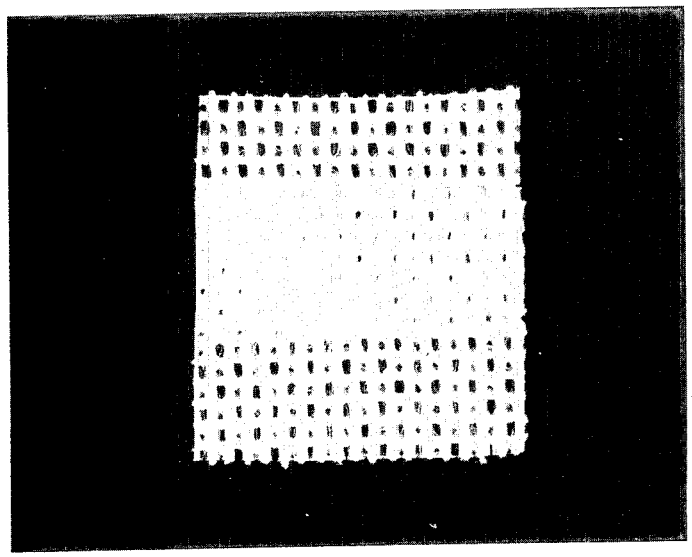
FIG. 3A is a photograph (taken to scale) of two overlapping sheets of the nonwoven polyester fabric of FIG. 1A which have been impregnated with an isocyanate functional polyurethane prepolymer (such that the prepolymer represents about 82% by weight), laminated, and cured with water to form a cured laminate.
Figure 3B:
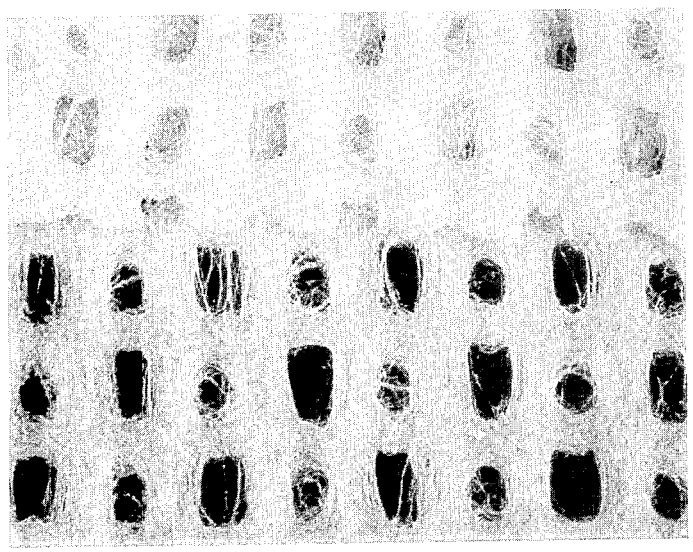
FIG. 3B is a photograph of a portion of the cured laminate of FIG. 3A shown at a magnification of five times (5×) that of FIG. 3A.
Figure 3C:
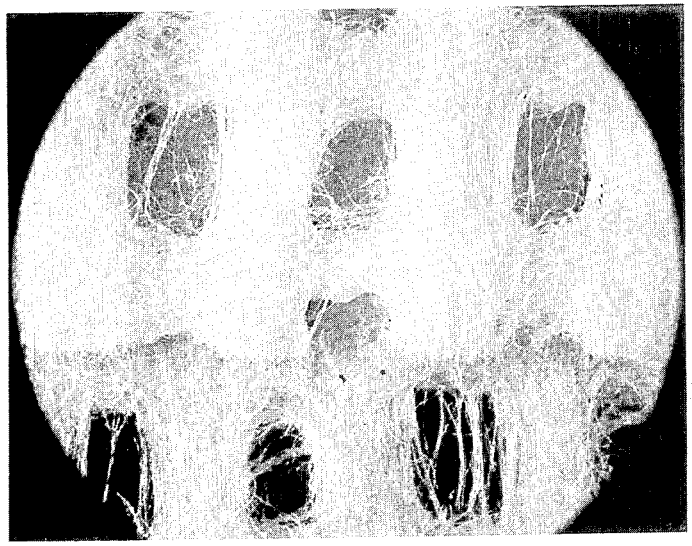
FIG. 3C is a photograph of a portion of the cured laminate of FIG. 3A shown at magnification of ten times (10×) that of FIG. 3A.

A sample of two resin impregnated sheets which were made in accordance with this Example 31, partially overlapped, and cured to form a laminate, is shown in FIGS. 3A-3C.

EXAMPLE 32

In Example 2, five resin impregnated strips (measuring 3 inches (7.6 cm) by 41 inches (184.1 cm)), prepared in accordance with Example 31, were removed from their pouches. These strips were dipped in water at room temperature for about 30 seconds, excess water was squeezed out, and each strip was wound around a 2 inch diameter mandrel covered with a stockinet so as to form a six layer ring therearound. After about 4 minutes, the rings were determined to have set sufficiently, and the rings were removed from the mandrels and allowed to cure for about 72 hours at a temperature of about 72° F. and 55% relative humidity.

Each of the cured rings of this Example 32 was placed in a compression test fixture on an Instron Model 1122 apparatus with a 100 lb. (453.6 kg) load cell, so that the overlap seam was not contacted by the penetrating bar of the compression test fixture. The compression test fixture had an upper and a lower base. The lower base was attached to the Instron Tensile Tester, and the upper base was attached to the load cell. The lower base was equipped with two rectangular metal bars dimensioned to approximately $\frac{3}{4}''$ (1.90 cm) wide, $\frac{1}{2}''$ (1.27 cm) thick, and 6'' (15.2 cm) long, and the bars were attached to the metal base about $1\frac{1}{2}''$ (3.81 cm) apart. Each cured ring was in turn placed on these bars and rested against the inside, rounded edges (having a radius of about $\frac{1}{8}''$ (0.381 cm)). The penetrating bar, approximately $\frac{1}{4}''$ (0.635 cm) wide, $\frac{3}{4}''$ (1.91 cm) thick, and 6'' (15.2 cm) long, was mounted to the upper base with a half round edge (having a radius of $\frac{1}{8}''$ (0.381 cm)) centered above and aligned parallel to the two bars on the lower base. The penetrating bar was lowered against the cured rings, and the maximum load sustained by the rings before failure was recorded.

Following the above procedure, the average ring strength of the rings of this Example 32 was determined to be about 32 lbs/inch (pounds per inch of cylinder length when using a cylinder 3 inches (7.6 cm) long and 2 inches (5.1 cm) in diameter or 5.72 kg/cm. Hence, this example evidences the good ring strengths which can be achieved using the orthopedic casting materials of the present invention.

EXAMPLE 33

In this example, several orthopedic casting materials within the scope of the present invention (having the same three dimensions set forth in Example 31) were prepared in accordance with the procedure and parameters set forth in Example 31 with the following exceptions. In this Example 33, a different nonwoven polyester fabric was employed. The fabric employed in Example 33 was obtained from E.I. duPont de Nemours and Company as Sontara® polyester fabric, conformable style 8043, set 2, 8 mesh, condition A. (This nonwoven polyester fabric is the subject of FIGS. 2A–2C herein.) Although this fabric also had about 64 apertures per square inch, the apertures were of two different sizes. In this regard, half of the apertures were about 3 mm×1.6 mm, while the other half of the apertures were measured to be about 1.6 mm×1.6 mm. This nonwoven polyester fabric had a basis weight of about 1.60 ounces per square yard (54.4 g/m²). This material was also observed to have an average fiber bundle cross-sectional area of about 0.77 mm², an average of about 480 fibers per fiber bundle along a given cross-section, an average fiber diameter of about 12 microns, and an average estimated void volume within each fiber bundle of about 92%. Further, the nonwoven polyester fabric had an extensibility of about 17% (when a 2 lb. (908 gram) load was applied across a 1.5 inch (3.8 cm) section of the fabric) in the elongated direction and an extensibility of about 21% (when a 2 lb. (908 gram) load was applied across a 1.5 inch (3.8 cm) section of the fabric) in the transverse direction. All of the other conditions of this Example 33 were identical to Example 31.

However, in this Example 33, after resin application, the average unoccluded area of the apertures of the resin impregnated strips was approximately 87%. Thus, the unoccludability of the apertures resulted in a material with excellent water vapor transition properties. Such air permeability demonstrates the ability of the fiber bundles to pull the resin within the interstices between fibers and thereby leave the apertures substantially unoccluded.

In this regard, when tested, cured ring laminates (having 6 layers, each measuring 2 inches (5.1 cm) by 2 inches (5.1 cm)) formed from the resin impregnated strips (measuring 3 inches (7.6 cm) by 41 inches (104.1 cm)) of this Example 33 were found to have an average passive water vapor permeability of about 2500 mg $H_2O$ vapor/m²-hr (when measured under an atmosphere of about 45% relative humidity and at a temperature of about 22° C.). Four cured flat laminates (having 6 layers, each measuring 2 inches (5.1 cm) by 2 inches (5.1 cm)) formed from one of the resin impregnated strips (measuring 2 inches (5.1 cm) by 48 inches (121.9 cm)) of this Example 33 were found to have an average air permeability of about 250 cm³ air/second when an air pressure differential of about 6.4 psi (absolute) or 449 g/cm² was imposed between the two sides of the laminate. Furthermore, following the procedure of Example 32, a cured six layer ring formed of the material of this Example 33 was found to have a ring strength of about 35 pounds/inch (6.26 kg/cm).

Figure 4A:
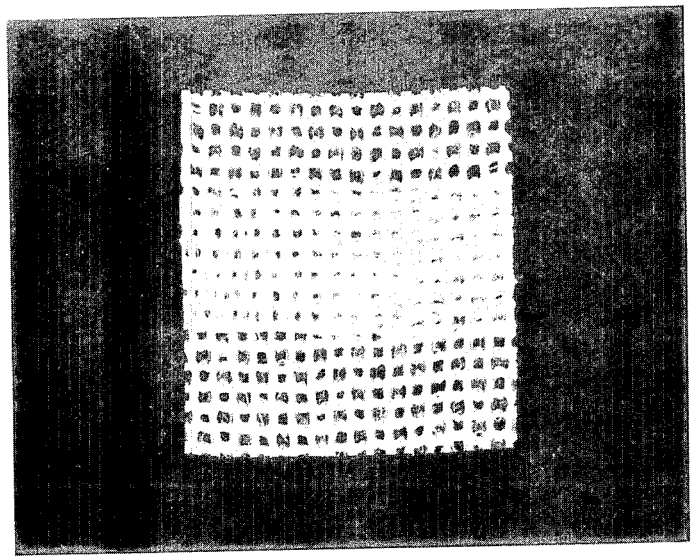
FIG. 4A is a photograph (taken to scale) of two overlapping sheets of the nonwoven polyester fabric of FIG. 2A which have been impregnated with an isocyanate functional polyurethane prepolymer (such that the prepolymer represents about 84% by weight), laminated, and cured with water to form a cured laminate.
Figure 4B:
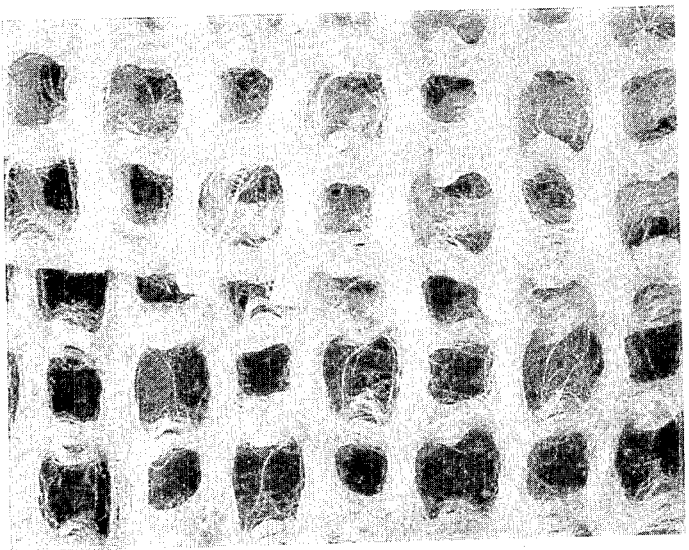
FIG. 4B is a photograph of a portion of the cured laminate of FIG. 4A shown at a magnification of five times (5×) that of FIG. 4A.
Figure 4C:
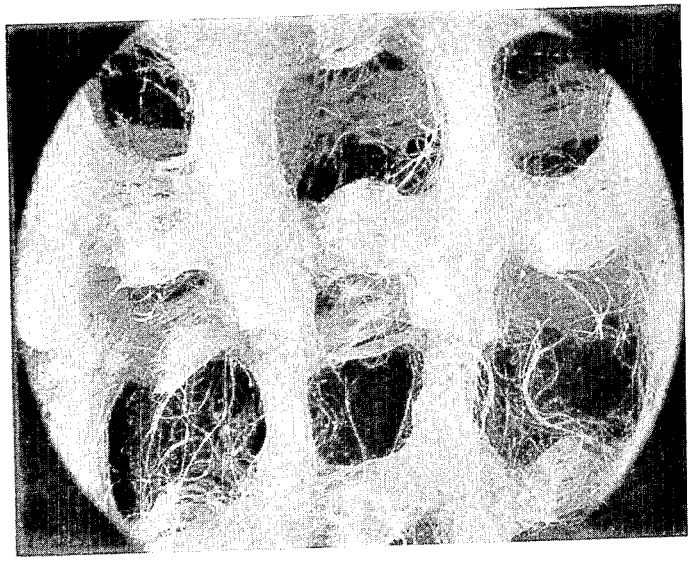
FIG. 4C is a photograph of a portion of the cured laminate of 4A shown at a magnification of ten times 10×) that of FIG. 4A.

A sample of two resin impregnated sheets which were made in accordance with this Example 33, partially overlapped, and cured to form a laminate, is shown in FIGS. 4A–4C.

EXAMPLE 34

In Example 34, a resin impregnated strip (measuring 3 inches (7.6 cm) by 144 inches (365.8 cm)) prepared in accordance with Example 33 was wound around a plastic core having a diameter of about 0.75 inches (1.9 cm), sealed in an airtight pouch, and the pouch was placed in an oven at a temperature of about 150° F. (65° C.) for about one week. After heating, the pouch was opened, and it was observed that relatively little resin had migrated through the rolled material, and virtually none had flowed off of the scrim. This evidences the enhanced ability of the orthopedic casting materials of the present invention to hold resin and to avoid undesirable migration and flow of the resin out of the material and onto the sides of the pouch during storage.

EXAMPLE 35

In this example, an orthopedic casting material (measuring 3 inches (7.6 cm) by 41 inches (104.1 cm)) within the scope of the present invention was prepared in accordance with the procedure and parameters set forth in Example 33 with the following exceptions. The nonwoven fabric employed in this Example 35 was made of Kevlar® polyarylamide fiber (instead or polyester fiber), obtained from E.I. duPont de Nemours and Company, Wilmington, Del. under the designation 039-8K, and had a basis weight of approximately 2.0 oz/sq yd (67.9 g/m²), an extensibility of about 13% in the elongated direction (when a 2 lb. (908 gram) load was applied across a 1.5 inch (3.8 cm) section of the fabric), and an extensibility of about 15% in the transverse direction (when a 2 lb. (908 gram) load was applied across a 1.5 inch (3.8 cm) section of the fabric). The unoccludability of the apertures was similar to that found in Example 33, resulting in a material with excellent water vapor transmission. When tested, a cured laminate of 6 layers of the orthopedic casting material of this Example 35 was found to have a passive water vapor permeability of about 2600 mg $H_2O$ vapor/$m^2$-hr when measured under an atmosphere of about 45% relative humidity and at a temperature of about 22° C. Furthermore, following the procedure of Example 32, a cured six layer ring formed of the material of this Example 35 was found to have a ring strength of about 33 pounds/inch (5.9 kg/cm).

EXAMPLE 36

In this example, an orthopedic casting material within the scope of the present invention may be prepared in accordance with the procedure of Example 31, using a nonwoven cotton fabric having properties as set forth in the above specification, instead of the polyester fabric of Example 31.

EXAMPLE 37

In this example, an orthopedic casting material within the scope of the present invention may be prepared in accordance with the procedure of Example 31, using a nonwoven nylon fabric having properties as set forth in the above specification, instead of the polyester fabric of Example 31.

EXAMPLE 38

In this example, an orthopedic casting material within the scope of the present invention may be prepared in accordance with the procedure of Example 31, using a nonwoven acrylic fabric having properties as set forth in the above specification, instead of the polyester fabric of Example 31.

EXAMPLE 39

In this example, an orthopedic casting material within the scope of the present invention may be prepared in accordance with the procedure of Example 31, using a nonwoven polypropylene fabric having properties as set forth in the above specification, instead of the polyester fabric of Example 31.

EXAMPLE 40

In this example, an orthopedic casting material within the scope of the present invention may be prepared in accordance with the procedure of Example 31, using a nonwoven fiberglass fabric having properties as set forth in the above specification, instead of the polyester fabric of Example 31. The fiberglass nonwoven fabric has a basis weight and is resin loaded within the parameters specifically set forth herein for fiberglass.

EXAMPLE 41

In this example, an orthopedic casting material within the scope of the present invention was prepared in accordance with Example 31 to provide a resin impregnated strip about 3 inches (7.6 cm) wide and about 144 inches (365.8 cm) long. Five strips, each having a length of about 14.5 inches (36.8 cm), were cut from this material, and were individually sealed in airtight pouches. Later, these five strips were removed from their respective pouches and tested according to the KCOF method set forth herein; the resin impregnated strips of this Example 41 were found to have a mean kinetic coefficient of friction of about 0.24.

EXAMPLE 42

In this example, orthopedic casting materials within the scope of the present invention were prepared in accordance with Example 31 measuring 3 inches (7.6 cm) by 144 inches (365.8 cm) and measuring 2 inches (5.1 cm) by 48 inches (121.9 cm), with the following exceptions. Instead of the resin disclosed in Example 31, the nonwoven polyester scrim was impregnated with the resin of Example 4 using the following procedure. A vessel containing about 4200 grams of the sulfonated urethane resin of Example 4 was heated to about 65° C. (150° F.) for about 12 hours, and about 148.5 grams of the heated sulfonated urethane resin was transferred to a 250 ml beaker to which 1.5 grams of MEMPE catalyst were added while mixing with a spatula. The resulting resin was immediately applied to each polyester scrim in the same amounts disclosed in Example 31.

Five resin impregnated strips, each having a length of about 18 inches (45.7 cm), were cut from the 144 inch (365.8 cm) length of material, and the individual strips were sealed in airtight pouches. Later, each of these five strips were removed from their respective pouches and tested in accordance with the KCOF method set forth herein; these five strips were found to have a mean kinetic coefficient of friction of about 0.23.

The 48 inch (121.9 cm) length of material was cured and tested for air permeability in accordance with the air permeability test set forth herein. When tested, four cured flat laminates formed from this material (each laminate having six layers, each layer measuring 2 inches (5.1 cm) by 2 inches (5.1 cm)) were found to have an average air permeability of about 91 $cm^3$ air/second when an air pressure differential of about 6.4 psi (absolute) or 449 g/$cm^2$ was imposed between the two sides of each laminate.

EXAMPLE 43

In this example, an orthopedic casting material within the scope of the present invention was prepared as follows. In Example 43, four strips about 3 inches (7.6 cm) wide and about 15 inches (38.1 cm) long and one strip about 2 inches (5.1 cm) wide and about 48 inches (121.9 cm) long of the nonwoven polyester fabric of Example 33 were impregnated with a resin having the following composition:

| Chemical | Weight % |
|---|---|
| Isonate 143L (Upjohn) | 55.07 |
| Benzoyl chloride | 0.05 |
| DB-100 silicone fluid (Dow Corning) | 0.18 |
| 2,6-Di-tert-tert-butyl-4-methyl phenol (BHT) | 0.48 |
| Niax PPG 725 (Union Carbide) | 42.47 |
| MEMPE catalyst | 1.75 |

The above-listed ingredients were combined and applied to the strips of nonwoven polyester fabric in accordance with the procedure of Example 31. Each strip was then sprayed on both surfaces with Tergitol TM NP-40 in accordance with the procedure of Example 22, and sealed in an airtight pouch. Later, the four 15 inch (38.1 cm) long strips were removed from their respective pouches and tested in accordance with the KCOF method set forth herein; these strips were found to have a mean kinetic coefficient of friction of about 0.29.

The 48 inch (121.9 cm) length of material was cured and tested for air permeability according to the air permeability test set forth herein. When tested, four cured flat laminates formed from this material (each laminate having six layers, each layer measuring 2 inches (5.1 cm) by 2 inches (5.1 cm)) were found to have an average air permeability of about 200 cm$^3$ air/second when an air pressure differential of about 6.4 psi (absolute) or 449 g/cm$^2$ was imposed between the two sides of each laminate.

EXAMPLE 44

In this example, a strip (about 3 inches (7.6 cm) wide and about 15 inches (38.1 cm) long) of the nonwoven Kevlar ® fabric of Example 35 was impregnated with the resin of Example 43 using the procedure of Example 43. However, in this Example 44, the resultant resin impregnated strip was coated with Cyanomer TM A370 in accordance with the procedure of Example 15. The resultant material was then tested in accordance with the KCOF method set forth herein; this material was found to have a kinetic coefficient of friction of about 0.27.

EXAMPLE 45

In this example, orthopedic casting materials within the scope of the present invention were prepared as follows. In this Example 45, one strip (about 3 inches (7.6 cm) wide and about 144 inches (365.8 cm) long), one strip (about 2 inches (5.1 cm) wide and about 48 inches (121.9 cm) long), and three strips (about 3 inches (7.6 cm) wide and about 41 inches (104.1 cm) long) of resin impregnated material were prepared in accordance with Example 31. Ten strips, each having a length of about 14.5 inches (36.8 cm), were cut from one of the 144 inch (365.8 cm) lengths of material; each of these ten strips was sprayed with polydimethylsiloxane in accordance with the procedure of Example 28 and individually sealed in an airtight pouch. Later, five of these strips were tested in accordance with the KCOF method set forth herein; these five strips were found to have a mean kinetic coefficient of friction about 0.22. The remaining five strips were tested according to the KCOF method set forth herein with the exception that the water dipping procedure (KCOF procedure steps 1 and 2) was omitted. In other words, these other five strips were tested in a "dry" state; the mean kinetic coefficient of friction of these five strips tested in the dry state was determined to be about 0.74.

The 48 inch (121.9 cm) length of material of this example was cured and tested for air permeability in accordance with the air permeability test set forth herein. When tested, four cured flat laminates formed from this material (each laminate having six layers, each layer measuring 2 inches (5.1 cm) by 2 inches (5.1 cm)) were found to have an average air permeability of about 115 cm$^3$ air/second when an air pressure differential of about 6.4 psi (absolute) or 449 g/cm$^2$ was imposed between the two sides of each laminate.

The 41 inch (104.1 cm) length of material of this example was tested for ring strength in accordance with the procedure set forth in Example 32. The average ring strength of the rings tested was determined to be about 30 pounds/inch (5.36 kg/cm).

From the foregoing, it is seen that the present invention provides nontacky orthopedic casting materials which do not employ plaster of Paris and yet exhibit good tactile manipulation and moldability during application so that the underlying bone structure of the limb can be properly palpated through the material during application. Further, the present invention provides nontacky orthopedic casting materials which preserve the advantages of non-plaster of Paris casting materials and which can be made to be less expensive than other non-plaster of Paris casting materials presently available.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An orthopedic support material, comprising a nonwoven, stretchable fabric impregnated with a prelubricated curable resin:
    wherein a major surface of the material exhibits a kinetic coefficient of friction of less than about 1.2;
    wherein said nonwoven fabric comprises a pattern of fiber bundles and apertures between said fiber bundles, each said fiber bundle comprising a plurality of fibers having interstices therebetween, the average cross-sectional area of each said fiber bundle being from about 0.2 mm$^2$ to about 1.2 mm$^2$; and
    wherein said resin is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material.

2. An orthopedic support material as defined in claim 1 wherein, prior to impregnation with said resin, said nonwoven fabric has from about 10% to about 45% extensibility in the elongated direction when a 2 pound load is applied across a 1.5 inch section of the nonwoven fabric.

3. An orthopedic support material as defined in claim 1 wherein the fibers in each said fiber bundle are oriented so as to be generally parallel to one another.

4. An orthopedic support material as defined in claim 1 wherein a cross-section of each said fiber bundle contains an average of at least about 100 of said fibers.

5. An orthopedic support material as defined in claim 1 wherein the average diameter of each individual fiber in each said fiber bundle is from about 1 micron to about 30 microns.

6. An orthopedic support material as defined in claim 1 wherein the average void volume within each said fiber bundle is from about 20% to about 98% of the total volume occupied by the fiber bundle.

7. An orthopedic support material as defined in claim 1 wherein the weight of said nonwoven fabric is from about 1 ounce per square yard to about 2.5 ounces per square yard.

8. An orthopedic support material as defined in claim 1 wherein said nonwoven fabric has from about 15 to about 400 of said apertures per square inch.

9. An orthopedic support material as defined in claim 1 wherein the average size of said apertures is from about 0.3 mm$^2$ to about 16 mm$^2$.

10. An orthopedic support material as defined in claim 1 wherein said nonwoven fabric is a spunlaced, hydroentangled, nonwoven fabric.

11. An orthopedic support material as defined in claim 1 wherein said nonwoven fabric comprises polyester.

12. An orthopedic support material as defined in claim 1 wherein said nonwoven fabric comprises cotton.

13. An orthopedic support material as defined in claim 1 wherein said nonwoven fabric comprises nylon.

14. An orthopedic support material as defined in claim 1 wherein said nonwoven fabric comprises acrylic.

15. An orthopedic support material as defined in claim 1 wherein said nonwoven fabric comprises polypropylene.

16. An orthopedic support material as defined in claim 1 wherein said nonwoven fabric comprises fiberglass.

17. An orthopedic support material as defined in claim 1 wherein said nonwoven fabric comprises polyarylamide.

18. An orthopedic support material as defined in claim 1 wherein said nonwoven fabric comprises carbon.

19. An orthopedic support material as defined in claim 1 wherein said resin is an isocyanate functional, polyurethane prepolymer resin.

20. An orthopedic support material as defined in claim 1 wherein sufficient resin is impregnated into the nonwoven fabric such that the resin represents from about 65% to about 90% by weight of the total weight of the orthopedic support material.

21. An orthopedic support material as defined in claim 1 wherein from about 0.1 grams to about 0.3 grams of resin are applied to each square inch of the nonwoven fabric.

22. An orthopedic support material as defined in claim 1 wherein from about 60% to about 100% of the total area of said apertures remains unoccluded after impregnation of said resin into said nonwoven fabric.

23. An orthopedic support material as defined in claim 1 wherein upon curing a laminate comprising 6 layers of said material said laminate has a passive water vapor permeability of at least about 2000 mg H$_2$O vapor/m$^2$-hr when measured under an atmosphere of about 45% relative humidity and at a temperature of about 22° C.

24. An orthopedic support material as defined in claim 1 wherein upon curing a laminate comprising 6 layers of said material, with each layer having an area of about 4 in$^2$, said laminate has an air permeability of from about 30 cm$^3$ air/second to about 370 cm$^3$ air/second when an air pressure differential of about 6.4 psi exists between two sides of the laminate.

25. An orthopedic support material as defined in claim 1 wherein after curing a ring laminate comprising 6 layers of said material and having a length of 3 inches and a diameter of 2 inches, said ring laminate has a ring strength of at least about 10 pounds per inch of ring length.

26. An orthopedic support material as defined in claim 1 wherein said prelubricated curable resin comprises a lubricant at the major surface of the material, said lubricant comprising
  (a) hydrophilic groups which are covalently bonded to the curable resin, or
  (b) an additive which is incompatible with the curable resin, or
  (c) a combination of (a) and (b);
and wherein said lubricant is present in an amount such that the kinetic coefficient of friction of the major surface of the material is less than about 1.2.

27. An orthopedic support material as defined in claim 26 wherein the lubricant comprises hydrophilic groups which are covalently bonded to the curable resin.

28. An orthopedic support material as defined in claim 27 wherein the lubricant comprises polyethylene oxide.

29. An orthopedic support material as defined in claim 27 wherein the lubricant comprises a polyethoxylated fatty alcohol.

30. An orthopedic support material as defined in claim 29 wherein the lubricant comprises sulfonate groups.

31. An orthopedic support material as defined in claim 28 wherein said lubricant is an additive which comprises a surfactant.

32. An orthopedic support material as defined in claim 31 wherein said surfactant is an alkyl, aryl, or aralkyl ionic compound.

33. An orthopedic support material as defined in claim 31 wherein said surfactant is an alkyl sulfate.

34. An orthopedic support material as defined in claim 31 wherein said surfactant is a polyethoxylated compound.

35. An orthopedic support material as defined in claim 31 wherein said surfactant is an anionic compound.

36. An orthopedic support material as defined in claim 31 wherein said surfactant is a nonionic compound.

37. An orthopedic support material as defined in claim 31 wherein said surfactant is a solid at ambient temperatures.

38. An orthopedic support material as defined in claim 26 wherein said lubricant is an additive which comprises a polymer having a plurality of hydrophilic groups.

39. An orthopedic support material as defined in claim 38 wherein said polymer is comprised of repeating units derived from ethylenically unsaturated monomers selected from the group consisting of acrylamide, vinylpyrrolidone, vinylacetate and its polymeric hydrolyzed derivatives, hydroxy and amino functional lower alkyl acrylates, and combinations thereof.

40. An orthopedic support material as defined in claim 38 wherein said polymer is polyvinyl alcohol.

41. An orthopedic support material as defined in claim 26 wherein said lubricant is an additive which comprises a polysiloxane.

42. An orthopedic support material as defined in claim 26 wherein said lubricant is an additive which comprises a polydimethylsiloxane.

43. An orthopedic support material as defined in claim 26 wherein said lubricant is an additive comprising a mixture of any of the compositions selected from the group consisting of:
  (i) a surfactant;

(ii) a polymer having a plurality of hydrophilic groups; and (iii) a polysiloxane.

44. An orthopedic casting material comprising a nonwoven sheet of polyester impregnated with a pre-lubricated, isocyanate functional, polyurethane prepolymer resin:

wherein a major surface of the material exhibits a kinetic coefficient of friction of less than about 1.2;

wherein said nonwoven sheet of polyester comprises a pattern of fiber bundles and apertures between said fiber bundles, each said fiber bundle comprising a plurality of fibers having interstices therebetween, the average cross-sectional area of each said fiber bundle being from about 0.2 mm$^2$ to about 1.2 mm$^2$, said nonwoven polyester sheet having from about 10% to about 45% extensibility along its length when a 2 pound force is applied across a 1.5 inch section of said sheet; and wherein said pre-lubricated, isocyanate functional, polyurethane prepolymer resin is impregnated into the interstices between said fibers of said fiber bundles in sufficient quantity such that the resin represents from about 65% to about 90% by weight of the total weight of the orthopedic casting material and imparts sufficient strength to the material upon curing to be used as an orthopedic casting material, said apertures remaining substantially unoccluded such that upon curing a laminate comprising 6 layers of said material said laminate has a water vapor permeability of at least about 2000 mg H$_2$O vapor/m$^2$-hr when measured under an atmosphere of about 45% relative humidity and at a temperature of about 22° C., thereby substantially avoiding skin maceration.

45. An orthopedic casting material as defined in claim 44:

wherein the fibers in each said fiber bundle are oriented so as to be generally parallel to one another and wherein a cross-section of each said fiber bundle contains an average of at least about 100 of said fibers;

wherein said nonwoven polyester sheet has a weight of from about 1 ounce per square yard to about 2.5 ounces per square yard; and wherein said nonwoven polyester sheet has from about 15 to about 400 of said apertures per square inch, the average size of said apertures ranging from about 0.3 mm$^2$ to about 16 mm$^2$.

46. A method of preparing an orthopedic support material, comprising the steps of:

providing a nonwoven, stretchable fabric comprising a pattern of fiber bundles and apertures between said fiber bundles, each said fiber bundle comprising a plurality of fibers having interstices therebetween, the average cross-sectional area of each said fiber bundle being from about 0.2 mm$^2$ to about 1.2 mm$^2$; and impregnating a curable resin into the interstices between the fibers of the fiber bundles so as to impart sufficient strength to the material upon curing to be used as an orthopedic support material while leaving the apertures between fiber bundles substantially unoccluded so as to permit sufficient water vapor permeability through the cured material, said curable resin being pre-lubricated such that, prior to the completion of curing, a major surface of the material exhibits a kinetic coefficient of friction of less than about 1.2.

47. An orthopedic support material, comprising a nonwoven, stretchable fabric impregnated with a pre-lubricated curable resin:

wherein a major surface of the material exhibits a kinetic coefficient of friction of less than about 1.2;

wherein said nonwoven fabric comprises a pattern of fiber bundles and apertures between said fiber bundles, each said fiber bundle comprising a plurality of fibers having interstices therebetween, the weight of said nonwoven fabric being from about 1 ounce per square yard to about 2.5 ounces per square yard; and wherein said resin is impregnated into the interstices between said fibers of said fiber bundles so as to impart sufficient strength to the material while leaving the apertures between fiber bundles substantially unoccluded so as to permit sufficient water vapor permeability through the cured material.

48. An orthopedic support material, comprising a nonwoven, stretchable fabric impregnated with a pre-lubricated curable resin:

wherein a major surface of the material exhibits a kinetic coefficient of friction of less than about 1.2;

wherein said nonwoven fabric comprises a pattern of fiber bundles and apertures between said fiber bundles, each said fiber bundle comprising a plurality of fibers having interstices therebetween;

wherein said resin is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material; and wherein upon curing laminate comprising 6 layers of said material said laminate has a passive water vapor permeability of at least about 2000 mg H$_2$O vapor/m$^2$-hr when measured under an atmosphere of about 45% relative humidity and at a temperature of about 22° C.

49. An orthopedic support material, comprising a nonwoven, stretchable fabric impregnated with a pre-lubricated curable resin:

wherein a major surface of the material exhibits a kinetic coefficient of friction of less than about 1.2;

wherein said nonwoven fabric comprises a pattern of fiber bundles and apertures between said fiber bundles, each said fiber bundle comprising a plurality of fibers having interstices therebetween;

wherein said resin is impregnated into the interstices between said fibers of said fiber bundles so as to impart sufficient strength to the material upon curing to be used as an orthopedic support material while leaving the apertures between fiber bundles substantially unoccluded so as to permit sufficient water vapor permeability through the cured material; and wherein upon curing a laminate comprising 6 layers of said material, with each layer having an area of about 4 in$^2$, said laminate has an air permeability of from about 30 cm$^3$ air/second to about 370 cm$^3$ air/second when an air pressure differential of about 6.4 psi exists between two sides of the laminate.

50. An orthopedic support material as defined in claim 1 wherein said major surface of the material exhibits a kinetic coefficient of friction of 0.93 or less.

51. An orthopedic support material as defined in claim 1 wherein said major surface of the material exhibits a kinetic coefficient of friction of 0.75 or less.

52. An orthopedic support material as defined in claim 1 wherein said major surface of the material exhibits a kinetic coefficient of friction of 0.4 or less.

* * * * *

UNITED STATES PATENT AND TRADEMARK OFFICE
CERTIFICATE OF CORRECTION

PATENT NO. : 4,856,502
DATED : August 15, 1989
INVENTOR(S) : Dean A. Ersfeld, et al.

It is certified that error appears in the above-identified patent and that said Letters Patent is hereby corrected as shown below:

Col. 1, Line 32, insert a period after "applier".
Col. 2, Line 52 "east" should be --cast--.
Col. 2, Line 66, after "sheet" insert --wherein a major--.
Col. 7, Line 29, "easting" should be --casting--.
Col. 7, Line 43, insert a period after --slippery--.
Col. 7, Line 47, insert a period after --tapes--.
Col. 8, Line 17, after "methyl" insert --, and--.
Col. 8, Line 54, "dimethylsiloxane-vinylmethYl" should be --dimethylsiloxane-vinylmethyl--.
Col. 8, Line 62, insert a period after "poly(chlorophenyl)-methylsiloxane".
Col. 8, Line 66, "g/m" should read --g/m$^2$--.
Col. 8, Line 66, delete the colon.
Col. 10, Line 14, "tothe" should be --to the--.
Col. 11, Line 57, "12,5000" should be --12,500--.
Col. 12, Line 7, insert a colon after "reasons".
Col. 12, Line 37, after "-OPO$_3$H," insert ---PO$_3$H,--.
Col. 12, Line 43, "g/m" should be --g/m$^2$--.
Col. 12, Line 55, "ba oteria" should be --bacteria--.
Col. 14, Line 22, "a" should be --as--.
Col. 14, Line 24, insert --B.-- before "Test".
Col. 14, Line 28, "pulley0.953" should be --pulley 0.953--.

UNITED STATES PATENT AND TRADEMARK OFFICE
CERTIFICATE OF CORRECTION

PATENT NO. : 4,856,502
DATED : August 15, 1989
INVENTOR(S) : Dean A. Ersfeld, et al.

It is certified that error appears in the above-identified patent and that said Letters Patent is hereby corrected as shown below:

Col. 14, Line 57, "cart should be --chart--.

Col. 14, Line 63, "1.10" should be --1.0--.

Col. 15, Line 26, insert --immediately upon-- before "immersion".

Col. 15, Line 49, insert a period after "8".

Col. 16, Line 10, after "morpholine" insert --)--.

Col. 17, Line 6, Delete "20".

Col. 17, Line 46, "g/m" should be --$g/m^2$--.

Col. 18, Line 14, "SCPTCHCAST" should be --SCOTCHCAST--.

Col. 19, Line 40-41, delete "onto casting tape as previous".

Col. 19, Line 40, after "coated" insert --onto casting tape as previously--.

Col. 19, Line 54, "sate" should be --state--.

Col. 20, Line 24, "ethlene" should be --ethylene--.

Col. 20, Line 25, before "from" insert --available--.

Col. 20, Line 54, "53.8 g/m:" should be --$3.8\ g/m^2$.--.

Col. 21, Line 48, delete "packaged according to".

Col. 21, Line 49, before "the" insert --The following resin was prepared, coated and packaged according to--.

Col. 21, Line 61, "206" should be --2.06--.

Col. 23, Line 24, "coating" should be --casting--.

Col. 23, Line 62, "one" should be --bone--.

Col. 25, Line 53, "2-2C should be --2A-2C--.

Col. 26, Line 54, "n" should be --an--.

UNITED STATES PATENT AND TRADEMARK OFFICE
CERTIFICATE OF CORRECTION

PATENT NO.   : 4,856,502

DATED        : August 15, 1989

INVENTOR(S)  : Dean A. Ersfeld, et al.

It is certified that error appears in the above-identified patent and that said Letters Patent is hereby corrected as shown below:

Col. 27, Line 10, "is" should be --it--.

Col. 28, Line 1,  insert a period after ")".

Col. 28, Line 35, delete "size of from".

Col. 28, Line 53, after "60" insert --%--.

Col. 29, Line 68, after "present" insert --invention,--.

Col. 31, Line 66, "polyarlamide" should be --polyarylamide--.

Col. 33, Line 4,  "prepare" should be --prepared--.

Col. 42, Line 55, delete the second occurrence of "-tert".

Col. 46, Line 2,  insert a colon after "comprising".

Col. 46, Line 23, "29" should be --27--.

Col. 46, Line 26, "28" should be --26--.

Col. 48, Line 17, after "material" insert --upon curing to be used as an orthopedic support material--.

Col. 48, Line 39, before "laminate" insert --a--.

Signed and Sealed this

Thirty-first Day of July, 1990

*Attest:*

HARRY F. MANBECK, JR.

*Attesting Officer*            *Commissioner of Patents and Trademarks*